(12) United States Patent
Davey et al.

(10) Patent No.: US 6,496,020 B1
(45) Date of Patent: Dec. 17, 2002

(54) METHOD AND APPARATUS FOR CAPACITANCE MEASUREMENT OF A DIELECTRIC MEDIUM UTILIZING THE RATIO OF CAPACITANCE MEASUREMENT MADE AT DIFFERENT FREQUENCIES

(75) Inventors: Christopher Lyndon Davey; Douglas Bruce Kell, both of Aberystwyth (GB)

(73) Assignee: University of Wales Aberystwyth, Dyfed (GB)

( * ) Notice: Subject to any disclaimer, the term of this patent is extended or adjusted under 35 U.S.C. 154(b) by 0 days.

(21) Appl. No.: 09/509,434

(22) PCT Filed: Sep. 28, 1998

(86) PCT No.: PCT/GB98/02918

§ 371 (c)(1),
(2), (4) Date: Apr. 21, 2000

(87) PCT Pub. No.: WO99/17124

PCT Pub. Date: Apr. 8, 1999

(30) Foreign Application Priority Data

Sep. 27, 1997 (GB) .............................................. 9720496

(51) Int. Cl.[7] .............................................. G01R 27/26
(52) U.S. Cl. ..................... 324/674; 324/667; 324/675; 324/682; 324/765; 324/678; 73/304 C
(58) Field of Search ................... 324/674, 667, 324/675, 682, 765, 678; 435/29, 287.1; 73/861, 304 C

(56) References Cited

U.S. PATENT DOCUMENTS

| | | | | |
|---|---|---|---|---|
| 3,665,302 A | * | 5/1972 | Lees et al. ................... | 324/717 |
| 3,684,953 A | * | 8/1972 | Grant ........................ | 324/667 |
| 4,151,457 A | * | 4/1979 | Rau ........................... | 324/324 |
| 4,208,624 A | * | 6/1980 | Miller ........................ | 324/682 |
| 4,240,027 A | * | 12/1980 | Larsen et al. ............... | 324/638 |
| 4,652,828 A | * | 3/1987 | Kenyon et al. .............. | 324/338 |
| 4,727,311 A | * | 2/1988 | Walker ....................... | 324/640 |
| 4,810,650 A | * | 3/1989 | Kell et al. ................ | 435/287.1 |
| 4,820,973 A | * | 4/1989 | Alvarez .................... | 73/304 C |
| 4,881,025 A | * | 11/1989 | Gregory .................... | 324/672 |
| 4,965,206 A | * | 10/1990 | Kell ........................ | 435/287.1 |
| 5,182,193 A | * | 1/1993 | Mishima et al. .............. | 435/29 |
| 5,269,175 A | * | 12/1993 | Chmiel et al. ............. | 73/53.05 |
| 5,351,558 A | * | 10/1994 | Horn et al. ............... | 73/861.08 |
| 5,371,039 A | * | 12/1994 | Oguro ........................ | 438/396 |
| 5,583,432 A | * | 12/1996 | Barnes ....................... | 324/204 |

FOREIGN PATENT DOCUMENTS

| | | |
|---|---|---|
| EP | 0 277 789 A2 | 2/1988 |
| GB | 1063515 | 10/1963 |
| GB | 2 298 046 | 8/1996 |
| WO | WO92/16835 | 10/1992 |
| WO | WO96/26438 | 8/1996 |
| WO | WO97/01090 | 1/1997 |

\* cited by examiner

*Primary Examiner*—N. Le
*Assistant Examiner*—Wasseem H. Hamdan
(74) *Attorney, Agent, or Firm*—David P. Gordon; David S. Jacobson; Thomas A. Gallagher

(57) ABSTRACT

A method for analyzing a dielectric medium comprises the step of measuring, at one or more frequencies, the capacitance between a pair of electrodes immersed in the dielectric medium. The proportion of the or each capacitance measurement due to electrode polarization capacitance and/or to the residual capacitance of the dielectric medium is then determined using capacitance measurements made between the electrodes at a first frequency and at a second frequency, the ratio of the respective polarization capacitances at these two frequencies being predetermined. An apparatus for performing the method is also disclosed.

19 Claims, 17 Drawing Sheets

METHOD AND APPARATUS FOR CAPACITANCE MEASUREMENT OF A DIELECTRIC MEDIUM UTILIZING THE RATIO OF CAPACITANCE MEASUREMENT MADE AT DIFFERENT FREQUENCIES

BACKGROUND OF THE INVENTION

1. Field of the Invention

The present invention relates to an apparatus for determining the capacitance of a dielectric medium.

2. State of the Art

The on-line and real-time measurement of the biomass content of fermentations is still an active area of research. New sensors are continuously being developed and the already established technologies are constantly being improved. The reason for this need for innovation is that the fermentation industry works with a very broad range of cell types using a very wide range of culturing conditions and under an ever-growing blanket of regulatory requirements.

To fit easily into an already-established fermentation installation, a biomass monitoring system must be generic and capable of working via the currently available probe ports, must not pose a significant contamination risk, be capable of withstanding in-situ the high temperatures and pressures or caustic nature of sterilisation processes, and the probe materials must be inert. The equipment must be supplied in a form that can easily be incorporated into (and survive in) a fermentation hall environment. This is true before any consideration can be given to its ability to work with the cell system being monitored.

The fermentation broth itself is a particularly hostile environment for any sensor to work in. The growth of the cells and the feeding and control regimes used ensure that it is an ever changing environment. The presence of vigorous and fluctuating aeration, and time-dependent temperature profiles, are a particular problem. The medium used can be highly viscous and often contains a wide range of non-biomass solids and immiscible liquids, particularly at the start of the fermentation. The medium's constitution can change markedly as the cells grow and consume its components.

An ideal measuring system should be capable of working with a wide variety of cell types, ranging from bacterial cells and yeasts, through filamentous fungi and bacteria to animal and plant cells, in both free and immobilised forms. The ability to measure a wide range of biomass concentrations is important, as is the inclusion of an in-situ cleaning system that can remove cellular growth on the sensing probe.

A widening body of literature has demonstrated that the measurement of biomass by use of a capacitive probe provides the best and most generic method in practical situations. Sensor methods based on two-pin electrodes and electromagnetic coupling are being developed but as yet have not been refined enough to work in anything other than laboratory model systems. The most highly developed technology that has found practical utility in industry is the Biomass Monitor (BM). This instrument fulfils the majority of the criteria outlined above and published work has shown it to work well for bacteria, yeast, filamentous fungi and bacteria, animal and plant cells, immobilised cells, for solid substrate fermentations of filamentous fungi, and in assessing cytotoxicity. Its major applications in industry so far have been for controlling the pitching of yeast slurries in brewing and for monitoring microbial fermentations in the pharmaceutical industry.

Details of biological dielectrics and the theory behind capacitive (dielectric) biomass measurements are well known to those skilled in the art. For the purposes of this specification a simplified heuristic model will be described. Cells in a suspension can be regarded as having a three-component structure. Outside and inside the cells is a conducting aqueous ionic medium, the former being the suspension medium the latter the cell cytoplasm. Surrounding the conducting cell core is the thin essentially non-conducting plasma membrane. This means that a cell suspension can be regarded, from an electrical point of view, as a suspension of spherical capacitors containing a conducting matrix surrounded by a conducting suspension medium. To make measurements on this system, an electric field is applied via a set of electrodes. The resulting electrical current paths have two routes through the suspension, either around the cells via the external conductance or through them via the membrane capacitance and internal and external conductances. At low radio-frequencies and below (<0.1 MHz), the cell membrane has a very low admittance, most of the current flows around the cells and, as the membrane capacitance is nearly fully charged, the capacitance of the suspension is very high. The more cells that are present per unit volume, the more spherical capacitors are charged and so the higher is the capacitance of the suspension. The low-frequency capacitance gives a measure of cellular volume fraction. As non-biomass material (including necromass) lacks an intact plasma-membrane, it does not give a significant capacitance contribution. At frequencies above 10 MHz, the membrane capacitance is shorted out, the induced charge held by the membranes is very low and so the capacitance of the suspension approaches that of the water in the suspending medium.

From these arguments, one expects the capacitance of a cell suspension to go from a high low-frequency plateau to a low high-frequency one. This fall in capacitance is called the β-dispersion (FIG. 1). The high-frequency residual capacitance due mainly to water dipoles is called $C_\infty$. The height of the low frequency plateau above $C_\infty$ is called the capacitance increment $\Delta C_\beta$ and its magnitude is proportional to the biomass content of the suspension. The frequency when the fall from $\Delta C_\beta + C_\infty$ to $C_\infty$ is half completed is called the critical frequency $f_c$. The steepness with which capacitance falls as frequency increases is described by the Cole-Cole α value. This has values in the range $0=<\alpha<1$ and is supposed to reflect the distribution of relaxation times in the suspension due to heterogeneity. Shown on FIG. 1 are the curves for α equals 0 (no distribution of relaxation times) and α equals 0.2. Increasing α from 0 does not change $\Delta C_{62}$, $f_c$ or $C_\infty$, its major effect on the a equals 0.2 plot shown on the figure is that in the frequency window shown the low-frequency plateau is not achieved.

From these arguments, one can see that to estimate the biomass in a fermentation broth, all that is necessary is to measure the $\Delta C_\beta$ of the suspension. On the BM this is done in either of two ways. FIG. 2 line (a) shows a β-dispersion with a spot measuring frequency typically 0.4 MHz) marked by an arrow and the capacitance at that frequency marked by a dot on the curve. As can be seen, the capacitance at the measuring frequency is a good approximation of the $\Delta C_\beta$ and hence biomass concentration. In reality, what is done for these single-frequency biomass measurements, and what has been done on this Figure, is to back off the capacitance due to the suspending medium to zero at the spot measuring frequency prior to inoculation. Then any change in the capacitance at that frequency reflect changes in $\Delta C_\beta$ and hence biomass concentration. The second capacitive biomass method uses two frequencies, the spot measuring frequency as before and also a high frequency reference (10 MHz). From FIG. 2 it will be seen that the difference in the capacitance between the spot measuring frequency (0.4 MHz) and that at 10 MHz also gives a good estimate of $\Delta C_\beta$.

For both methods to work reliably the spot biomass measuring frequency should be well into the low-frequency plateau of the β-dispersion, since the $f_c$ of the dispersion can move with changes in the medium conductance. If the measuring frequency were on the falling part of the dispersion, then movements in the $f_c$ could cause significant changes in the capacitance measured at the spot frequency and result in corresponding errors in the biomass determination.

To be well onto the plateau means that for most β-dispersions it is necessary to use a measuring frequency below 0.5 MHz. However, this forces the use of a frequency region in which the polarisation of the measuring electrodes can contribute a significant capacitance which interferes with the biomass measurements. This electrode polarisation effect results largely from the charged electrodes attracting around themselves a counter layer of ions which acts electrically as a capacitor/resistor network in series with the biological suspension one is trying to measure.

For a given electrode material, the most important factor that controls the magnitude of this electrode polarisation is the conductance of the suspending medium: the higher the conductance the larger the polarisation, until it completely swamps the β-dispersion. Line (b) on FIG. 2 shows the β-dispersion curve in (a) but with the small amount of polarisation typical of most fermentations. At the spot measuring frequency, the polarisation's contribution to the signal is quite low and does not result in a significant error in biomass estimation. The real problems occur when the medium conductance is very large and the biomass concentration is comparatively low. This is illustrated by line (c) on FIG. 2, where the β-dispersion line (a) has been swamped by polarisation. Under these conditions, the polarisation results in a large error in the estimated biomass concentration using the spot measuring frequency. Since the magnitude of this polarisation can be time-dependent as the medium conductance changes or as the electrodes become fouled, it is clear that dielectric biomass estimation can be rendered much more difficult.

A variety of methods have been used in the past to remove the electrode polarisation's contribution to biological capacitance spectra. These include:

(1) Taking measurements with different distances between the measuring electrodes whilst keeping the electrode surface current density constant. As the distance changes, the electrode polarisation's impedance remains the same whilst the suspension's impedance changes, enabling the polarisation's contribution to the signal to be eliminated. This method is impractical for on-line biomass measurements as it involves introducing potentially unreliable moving parts into the fermenter.

(2) Making a frequency scan of the β-dispersion with the electrode polarisation present. Non-linear least squares curve fitting is then used to fit the data to the Cole-Cole equation for the β-dispersion and a term modelling the polarisation. This gives a best estimate value for $\Delta C_\beta$ which can be used for biomass estimation. For the BM, the limited frequency range (0.2 to 10 MHz) combined with some residual uncompensated inductances at the higher frequencies means that this method ceases to be reliable under conditions of large polarisation.

(3) The polarisation control method is frequently used for off-line measurements made on the BM. This involves doing a frequency scan of the cell suspension whilst noting down the *conductance at the lowest frequency used. A sample of the suspending medium is then taken and its conductance adjusted, at the lowest frequency, to that of the suspension using distilled water or potassium chloride solution (KCl). A scan of this solution gives an estimate of the polarisation which can subsequently be subtracted from the cell suspension scan to give data largely free from polarisation. This method, however, cannot be put on-line in a fermenter.

(4) Electromagnetically coupled electrodes can eliminate the need for actual physical contact between the metal used in the measuring system and the aqueous ionic suspension medium, thus removing polarisation completely. Although such systems do exist, none of them as yet have been developed enough to be a useful proposition in a real fermentation environment.

(5) Non-polarisable electrodes can be used and indeed the BM used solid pure gold electrode pins. As will be shown later, the recent move to platinum pins for BM probes will result in significant reductions in electrode polarisation. Even platinum, however, does not reduce polarisation enough to allow reliable measurements at very high conductances with a relatively low biomass concentration present.

(6) The BM's main method of reducing electrode polarisation is the use of a four-electrode pin system. The two outer pins are used to drive current through the sample, whilst the two inner pins are used to detect the potential drop across the suspension that this induces. This potential is detected with a very high impedance voltmeter system which means that virtually no current flows across the inner pins' electrode/solution interfaces. As it is such a current flow that causes the polarisation, then its elimination also removes the polarisation problem. In reality, the four-terminal electrode configuration works well when compared to say a pair of platinum blacked platinum pins, but it does not remove all the polarisation, especially in highly conducting media.

The BM's phase detector system is quite capable of accurately detecting quite small capacitance values in the presence of a large conductance. What limits its use, at the high conductances found in animal cell suspensions and in some microbial broths, is the electrode polarisation present. For suspensions with a high biomass content, as in some immobilized systems or high-density cultures, electrode polarisation is not a significant problem even at high conductances. Where a new polarisation elimination method would be useful is in those situations where the β-dispersion curve has become embedded in a large polarisation curve because the biomass concentration is relatively low.

The object of the present invention is to address the above-noted problem.

SUMMARY OF THE PRESENT INVENTION

In accordance with the present invention, there is provided a method for analysing a dielectric medium, said method comprising the steps of measuring, at one or more frequencies, the capacitance between a pair of electrodes immersed in said dielectric medium and determining the proportion of the or each capacitance measurement due to electrode polarisation capacitance and/or to the residual capacitance of the dielectric medium using capacitance measurements made between said electrodes at a first frequency and at a second frequency, the ratio of the respective polarisation capacitances at these two frequencies being pre-determined.

We have established experimentally that capacitance due to electrode polarization is only significant over a frequency range within which the residual capacitance level is substantially constant. Therefore, preferably said first and second measurement frequencies lie within the range over which it is assumed that said residual capacitance level (Cres) is substantially constant.

Assuming the residual capacitance level to be constant, the capacitance measurements made at said first and second measurement frequencies allow this residual capacitance level to be calculated, as well as the respective electrode polarisation capacitances at said first and second measurement frequencies.

The calculated residual capacitance value may be sufficient to establish the biomass content of the dielectric medium. However, we have also established experimentally that a relationship of the form $Cpol=Af^p$ exists between electrode polarisation capacitance Cpol and frequency f, where A and p are constants. Therefore, having determined the respective electrode polarisation capacitances at said first and second measurement frequencies, these values may then be substituted into the above equation so that the capacitance due to electrode polarisation may be estimated for any frequency.

Thus, said one or more frequencies may comprise said first and second measurement frequencies. However, said one or more frequencies preferably comprise frequencies other than said first and second frequencies, which other frequencies are preferably greater than said first and second frequencies.

We have further established experimentally that, where the conductance of the dielectric medium exceeds a certain level, the value p is substantially constant for varying conductance.

Thus, the value of p may be estimated using known techniques applied to experimental data obtained for a control medium which preferably comprises a highly conducting, purely aqueous ionic solution. The value p may then be substituted into the above equation to determine appropriate values for said first and second measurement frequencies which provide the required polarisation capacitance ratio.

Alternatively, appropriate values for said first and second measurement frequencies may be determined for the control medium by estimating the polarisation capacitance at a first measurement frequency using known techniques and then varying the measurement frequency to identify the frequency at which the estimated polarisation capacitance has varied by the required amount.

Where p is constant, so too is the ratio between the respective polarisation capacitances at said first and second measurement frequencies. Therefore, an identical polarisation capacitance ratio may be assumed for the same two measurement frequencies at all conductance values exceeding a certain limit, and so appropriate first and second measurement frequencies need only be determined once.

In those circumstances in which the residual capacitance level is not substantially constant, we have found from our experiments that the magnitude of the offset capacitance varies substantially linearly with frequency.

In this case, in order to derive the parameters of the expression representing the relationship between said electrode polarisation capacitance and frequency, preferably one or more additional capacitance measurements are made within the range over which it is assumed that said residual capacitance level varies substantially linearly with frequency.

Also in accordance with the present invention, there is provided an apparatus for measuring, at said one or more frequencies, the capacitance between a pair of electrodes immersed in a dielectric medium and for determining the proportion of the or each capacitance measurement due to electrode polarisation capacitance and/or to the residual capacitance of the dielectric medium using capacitance measurements made between said electrodes at a first frequency and at a second frequency, the ratio of the respective polarisation capacitances at these two frequencies being pre-determined.

Figure 14A:
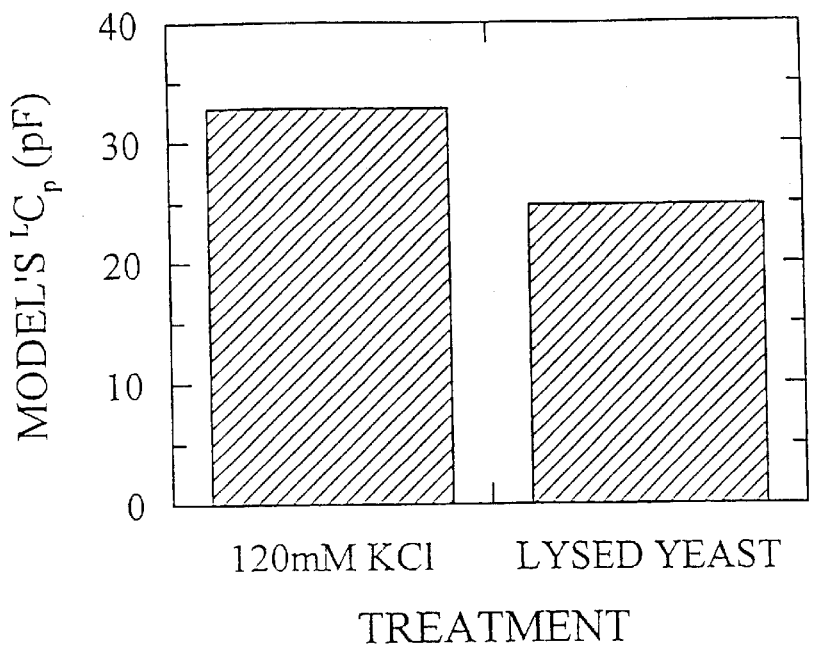
Figure 14B:
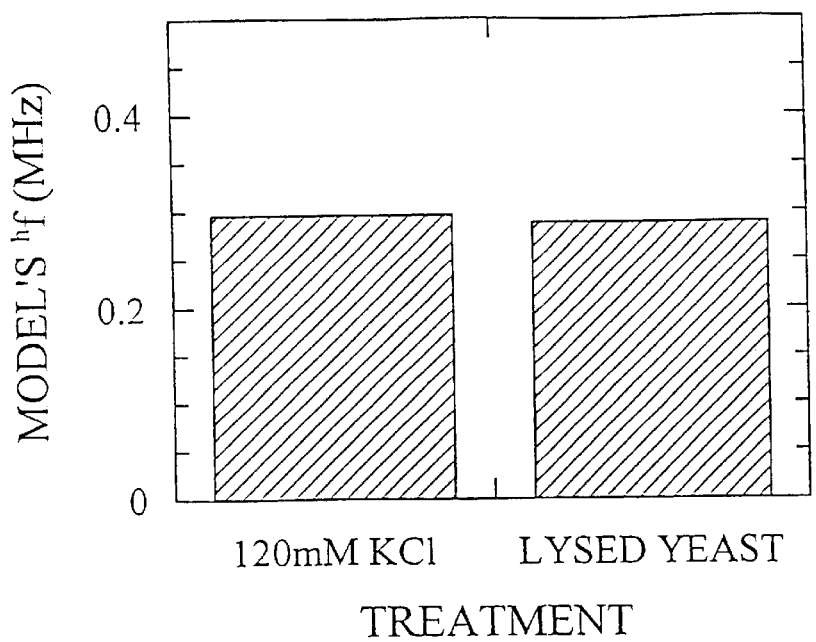
Figure 15A:
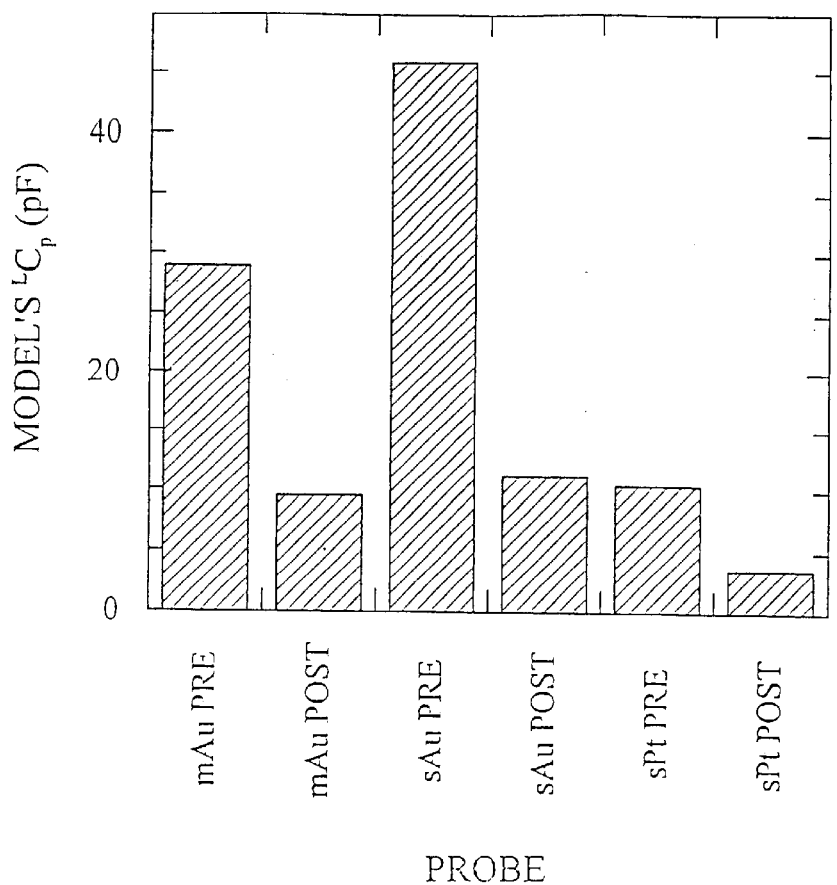
Figure 15B:
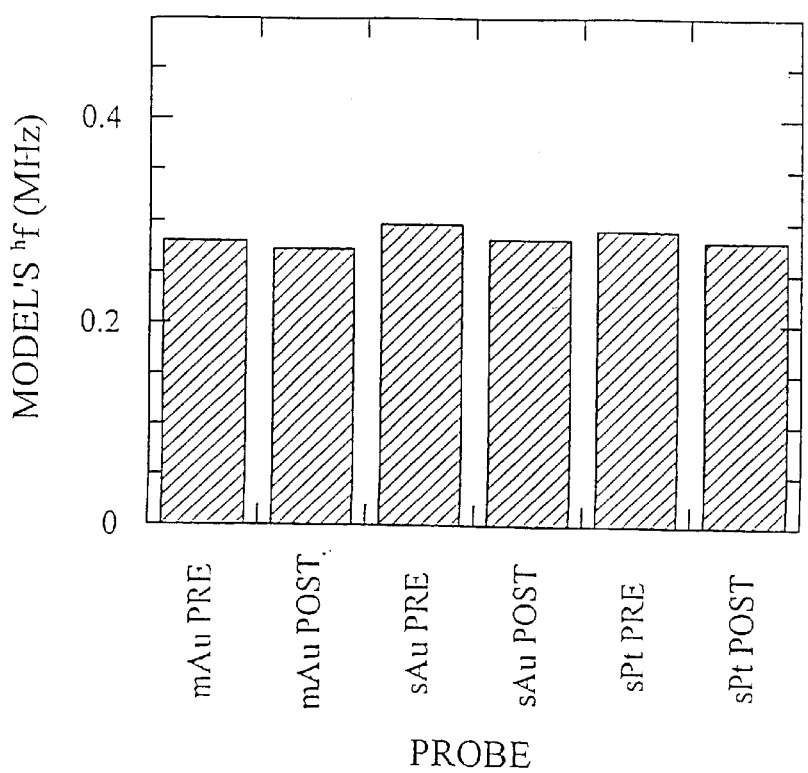
Figure 16A:
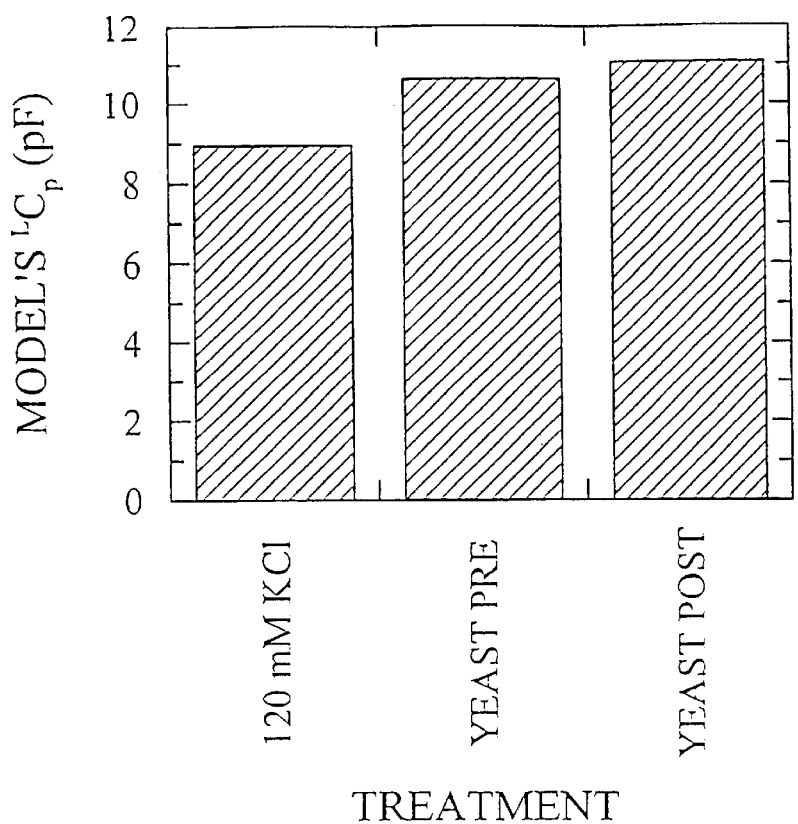
Figure 16B:
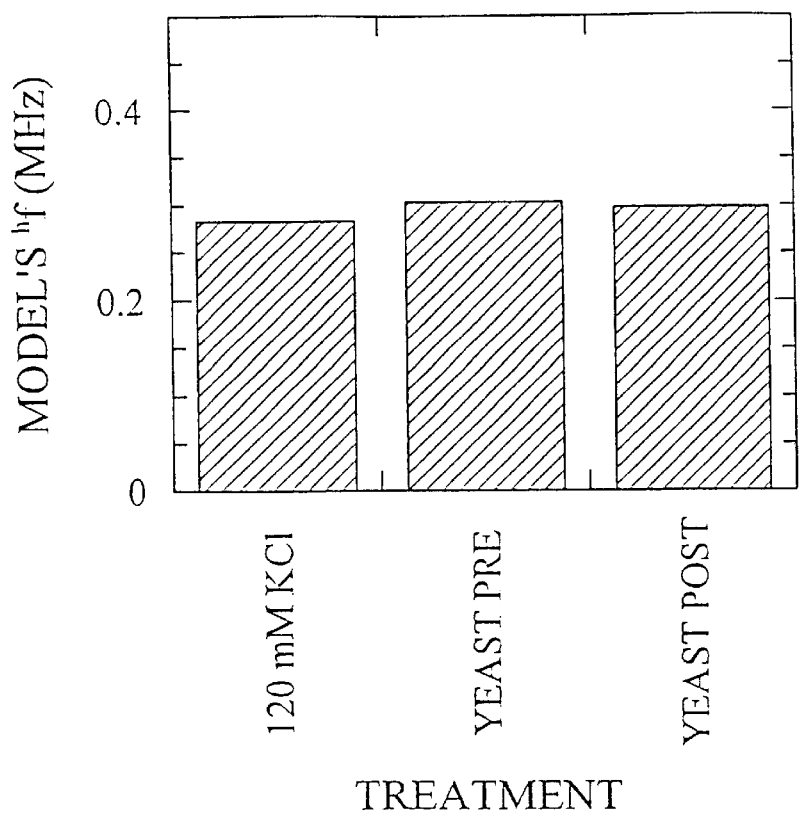
Figure 17:
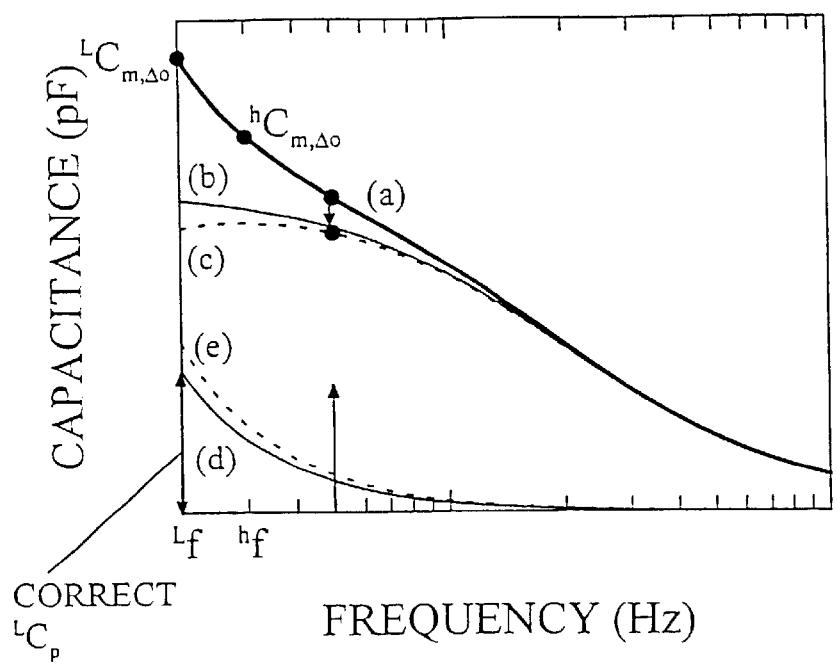
Figure 18A:
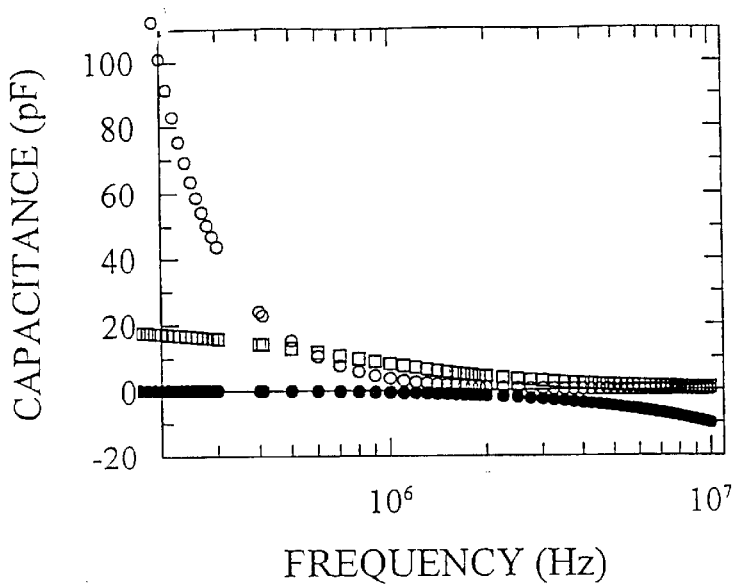
Figure 18B:
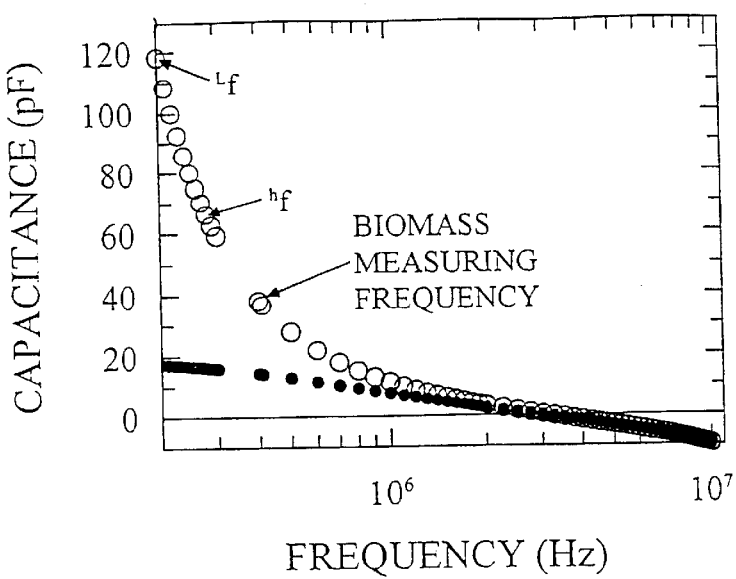
Figure 18C:
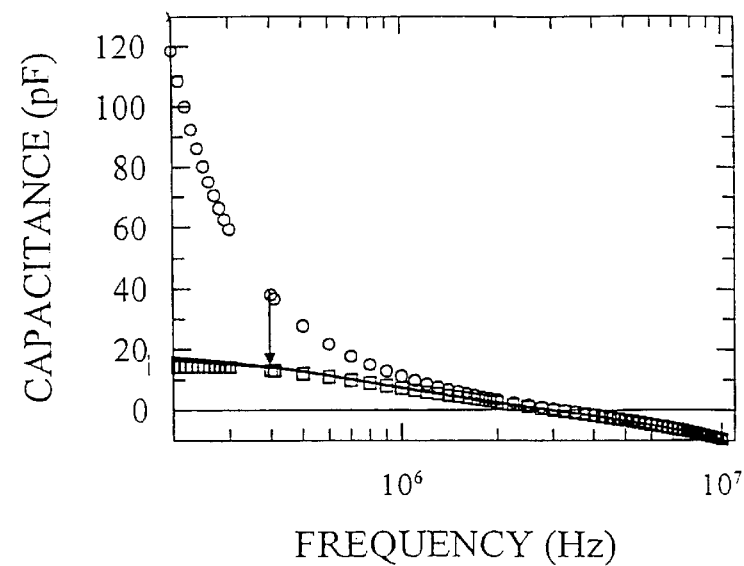
Figure 19A:
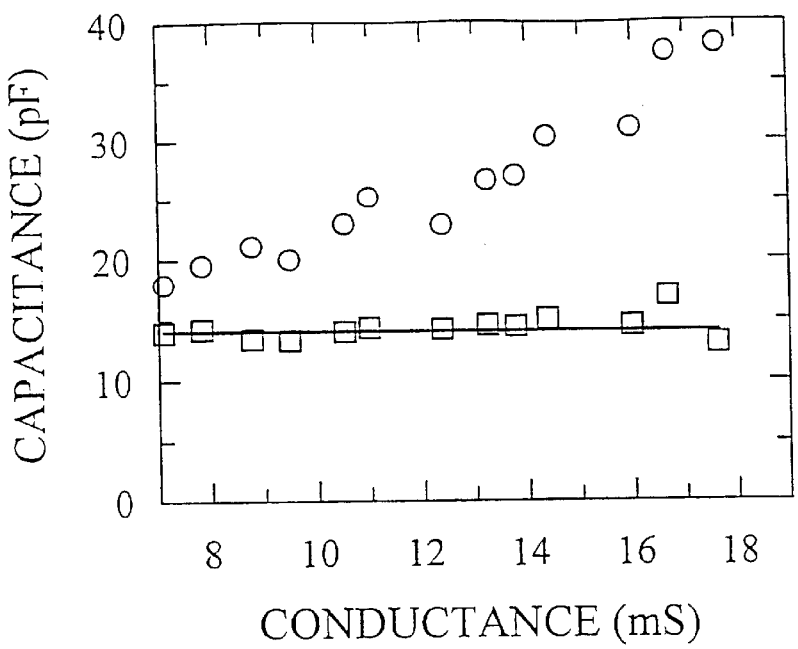
Figure 19B:
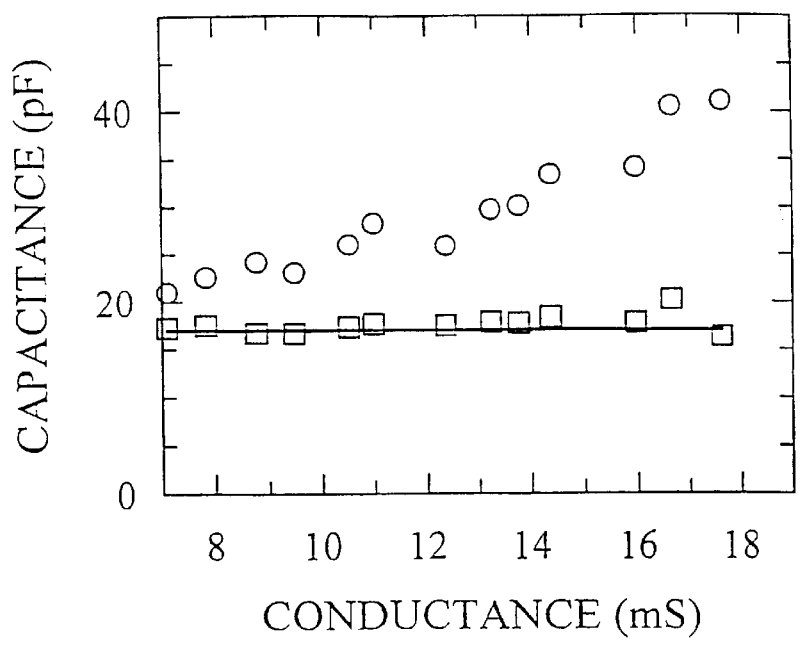
Figure 20A:
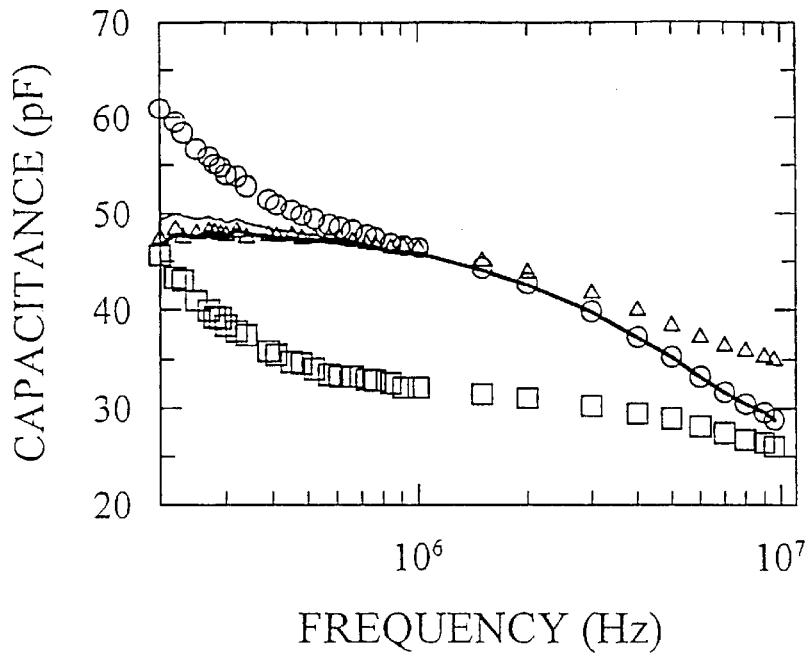
Figure 20B:
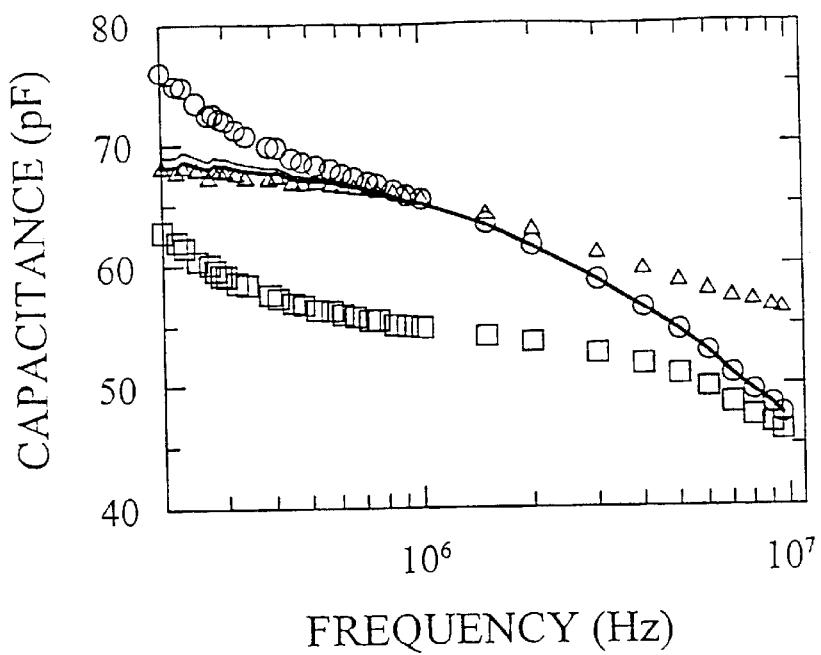
Figure 21:
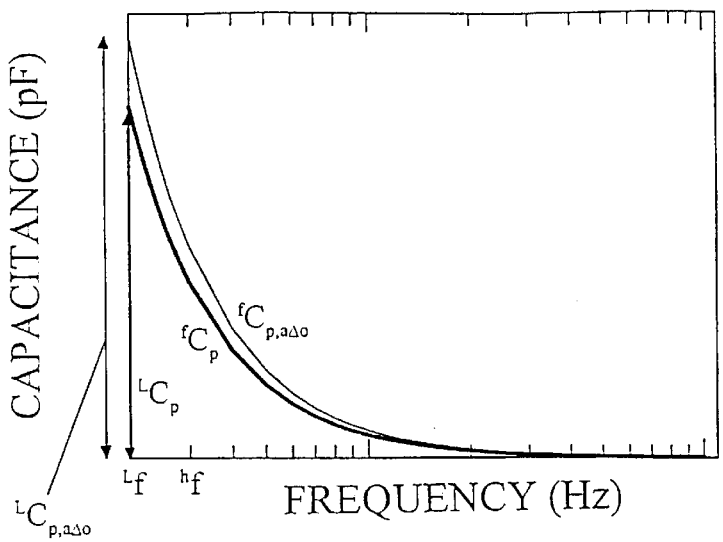
Figure 22:
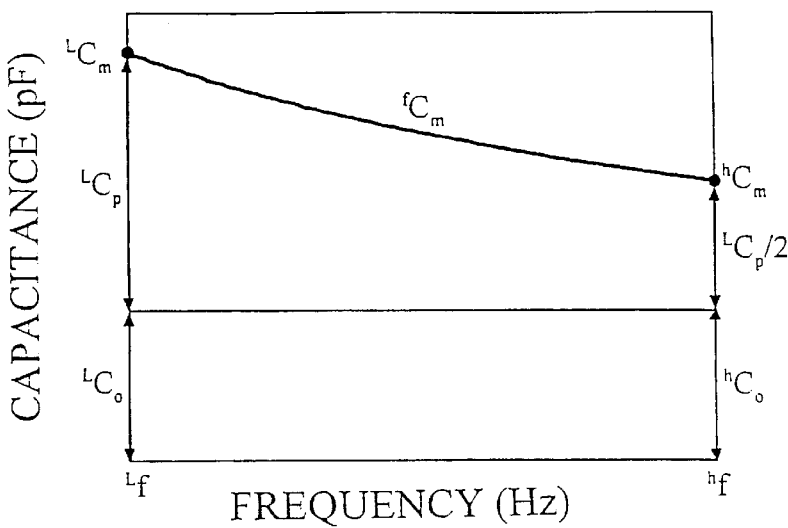
Figure 23:
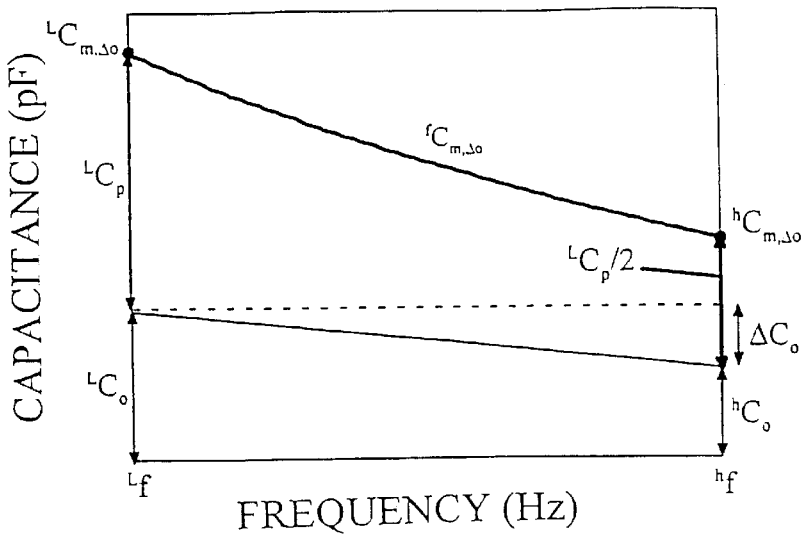
Figure 24:
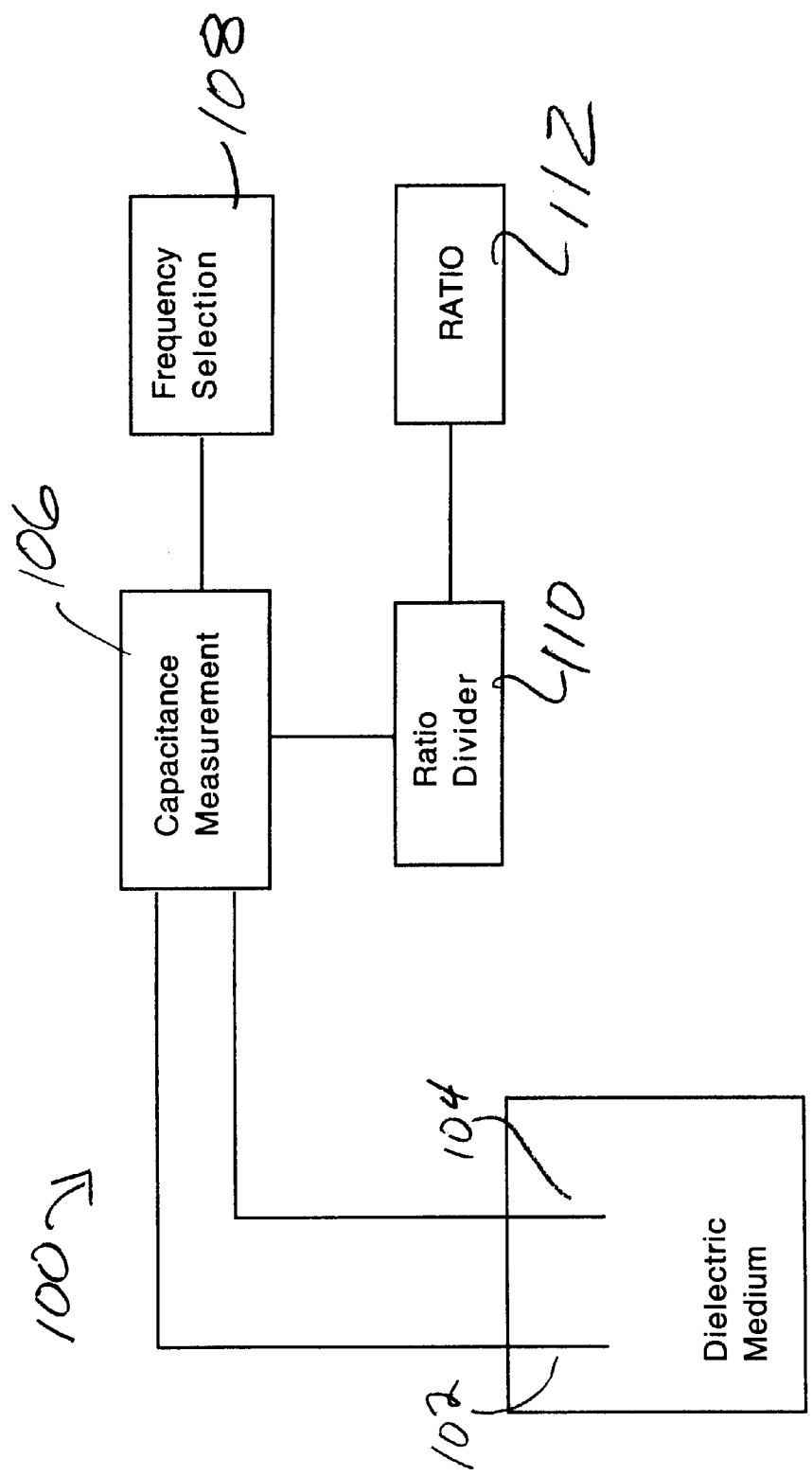

FIG. 14a a graph illustrating the influence of electrode fouling by a lysed yeast suspension on $^L C_p$;

FIG. 14b is a graph illustrating the influence of electrode fouling by a lysed yeast suspension on $^h f$;

FIG. 15a is a graph illustrating the $^L C_p$ of gold (Au) and platinum (Pt) electrodes before ("PRE") and after ("POST") electrolytic cleaning;

FIG. 15b is a graph illustrating the $^hf$ of gold (Au) and platinum (Pt) electrodes before ("PRE") and after ("POST") electrolytic cleaning;

FIG. 16a is a graph illustrating he $^LC_p$ of a gold electrode before ("PRE") and after ("POST") electrolytic cleaning in a lysed yeast suspension;

FIG. 16b is a graph illustrating the $^hf$ of a gold electrode before ("PRE") and after ("POST") electrolytic cleaning in a lysed yeast suspension;

FIG. 17 is a graph illustrating the effect of a sloping offset capacitance between $^Lf$ and $^hf$ on the results of applying the 2f model;

FIG. 18a is a graph illustrating the BM baseline (closed circles), β-dispersion (squares) and electrode polarization (open circles) data used in one of the simulations;

FIG. 18b is a graph illustrating the offset data (closed circles) and test suspension data (open circles) generated from the plots of FIG. 18a;

FIG. 18c is a graph illustrating the results of applying the 2f method to the test suspension data of FIG. 18b;

FIG. 19a is a graph illustrating the removal of electrode polarization at a single spot biomass measuring frequency when the β-dispersion's $f_c$ is low, as a function of the conductance of the simulated suspension;

FIG. 19b is a graph illustrating the removal of electrode polarization at a single spot biomass measuring frequency when the β-dispersion's $f_c$ is high, as a function of the conductance of the simulated suspension;

FIG. 20a is a graph illustrating the effects of the application of the 2f method and the use of polarization control data on the capacitance spectrum of a yeast suspension in the high cell constant mode of a BM;

FIG. 20b is a graph illustrating the effects of the application of the 2f method and the use of polarization control data on the capacitance spectrum of a yeast suspension in the low cell constant mode of a BM;

FIG. 21 is a graph illustrating the effect of offset error on the electrode polarization curve given by the 2f method;

FIG. 22 is a graph illustrating a capacitance spectrum between $^Lf$ and $^hf$ when the offset capacitance is constant between the two frequencies;

FIG. 23 is a graph illustrating a capacitance spectrum between $^Lf$ and $^hf$ when the offset capacitance is not constant between the two frequencies; and FIG. 24 is a simplified block diagram illustrating an apparatus according to the invention.

EXAMPLE

The following is an example to illustrate the manner in which the capacitance of a dielectric medium can be measured using an apparatus in accordance with the present invention.

A first capacitance measurement ($Ctot_1$) is made at a first frequency ($f_1$), and a second capacitance measurement ($Ctot_2$) is made at the frequency ($f_2$) at which the capacitance due to electrode polarisation at said first frequency ($Cpol_1$) is assumed to have decreased by a pre-determined amount, preferably 50 percent.

The unknown parameters A and p of the expression relating electrode polarisation capacitance (Cpol) to frequency (f) may thus be obtained as follows Using firstly the fact that total capacitance ($Ctot_x$) at a particular frequency ($f_x$) is equal to the residual capacitance ($Cres_x$) plus the electrode polarisation capacitance ($Cpol_x$), secondly the fact that the residual capacitance ($Cres_x$) is assumed to be constant in the region of interest, and thirdly the fact that the electrode polarisation capacitance at $f_2$ ($Cpol_2$) is equal to half that at $f_1$ ($Cpol_1$), the simultaneous equations $$Ctot_1 = Cres + Cpol_1$$

$$Ctot_2 = Cres + (0.5 \times Cpol_1)$$

may be solved to obtain Cres, $Cpol_1$ and $Cpol_2$.

The value Cres derived above may be sufficient to estimate the biomass content of the sample, however, the values of $Cpol_1$ and $Cpol_2$, together with their associated frequencies $f_1$ and $f_2$, may be substituted into the equation $$Cpol_x = Af_x^p$$

to obtain the unknown parameters A and p, so that the capacitance due to electrode polarisation may be estimated for any frequency.

Experiments

In the following, we give a detailed report of experiments which we have carried out and on which the invention is based.

Methods

Chemicals and yeasts used

All the salts were of analytical grade and all solutions and suspensions were made up in distilled water. The salt solutions used, other than KCl, were adjusted to the same 1 MHz conductance as 120 mM KCl (with the BM in high cell constant mode) with the relevant solid salt.

A totally lysed yeast suspension was made using a variety of lytic stresses, as previous experiments had shown that this was the only way to ensure complete cell lysis and hence no β-dispersion. The suspension was made as follows: Allinsons Dried Active Baking Yeast was obtained locally and made up in distilled water to give a suspension dry weight of 101 mg/ml. This was then boiled for 70 minutes over a Bunsen burner, cooled and frozen. The next day the suspension was thawed and diluted with distilled water to give an equivalent dry weight of 35 mg/ml. The suspension was then autoclaved for minutes at 15 lb/in$^2$ before being cooled and refrozen. On the day of use, the yeast was thawed, allowed to reach room temperature and diluted 1 in 3 in 120 mM KCl before its conductance was adjusted to that of 120 mM KCl (at 1 MHz, with the BM in high cell constant mode) using solid KCl or distilled water.

The living yeast suspensions used were made using fresh baker's yeast paste obtained locally. When the BM was in high cell constant mode the yeast was made up in 140 mM KCl, in low cell constant mode 70 mM was used. The suspensions were made as follows. (1) The extent of electrode polarisation in the relevant KCl solution was estimated by measuring the difference in capacitance between 0.2 and 1 MHz. (2) The BM was then set to 0.4 MHz and yeast paste added and suspended until the capacitance had increased by between one half and one times the estimated polarisation magnitude. (3) The suspension was then left an hour to stabilise. This resulted in a suspension where the yeast β-dispersion was well-embedded in the electrode polarisation but was still visible under it.

Electrodes and their preparation

The same three standard 25 mm diameter BM electrodes were used throughout the experiments. Two probes had solid pure gold pins while the other had pins of solid pure platinum. One gold probe had been used extensively and had developed a thin layer of amorphous gold on its pin surfaces, giving them a matt finish. This probe was thus called the mAu probe. The second gold pin probe was brand new and had electrode pins with smooth shiny surfaces and so was called the sAu probe. The platinum probe was also new and had smooth shiny pins; it was called the sPt probe.

Electrode polarisation is very sensitive to electrode fouling and so, before each experiment, the probes were cleaned very thoroughly using the following procedure, which we found to be reliable. (1) Rinse probe and pins with running cold tap water followed by rubbing the pins down with washing-up liquid (using a paper towel) and then rinsing as before. (2) Next the probe was treated with Concentrated Persil Colour (with stain release system) clothes washing liquid (Lever Brothers Ltd). This contains soap and polycarboxylates (<5%); nonionic surfactant (5 to 15%); anionic surfactant and zeolite (15 to 30%); protease; lipase; amylase and cellulase. 0.6 ml of the Persil was added to 100 ml of tepid tap water and the probe suspended in it for 5 minutes. The pins were then rubbed down with a paper towel and the diluted Persil before re-immersing for a further 5 minutes. (3) Rinse thoroughly in running cold tap water followed by a rinse in distilled water. The pins were then inspected to ensure that they were free from any adhering material.

Before and during the experiments, the probes were never allowed to dry out. If storage was required during an experiment, the probes were suspended in distilled water. Before such storage and between transfers to different treatments during the experiments, the electrodes were washed in distilled water. At the end of each experiment, the probes were washed in distilled water and stored dry under cover to keep dust off the pins.

Electrical measurements

All electrical measurements were made with the same Biomass Monitor 214A dielectric spectrometer (Aber Instruments Ltd., Science Park, Aberystwyth, Ceredigion SY23 3A, UK). Unless otherwise stated the BM was configured with low-pass noise filtration off, single frequency/scanning mode active, display and output set to absolute capacitance ("C mode"), the high cell constant mode set and the electrolytic cleaning system deactivated.

For all the experiments on salt solutions and lysed yeast suspensions, the BM was set to high cell constant mode and run under computer control using a program called BMScan. This was written in-house in the Microsoft QuickBasic 4.5 compiler and allowed the BM to be controlled, and data retrieved, via a DT2811 PGH A/D, D/A converter card (Data Translation Ltd, The Mulberry Business Park, Wokingham, Berkshire RG41 2GY, UK) in a 486 IBM compatible PC. The program was configured to scan the BM through the same 50 frequencies for each experimental run. These frequencies were picked by the program so that they were evenly spaced on a log frequency scale between 0.2 and 10 MHz. The order in which the 50 frequencies were scanned was randomised by the program so that each scan used a different ordering. During a scan, the program waited 4.5 seconds after switching frequencies for the BM to settle before taking and averaging 10 replicate readings at 0.1 seconds apart. For all experiments, the BM had been set-up and left on for several hours prior to use, to allow it to warm up properly.

The experiments on live yeast (and their polarisation controls) used 33 frequencies which were picked to place the majority of the data points in the frequency region where the polarisation and yeast β-dispersion overlapped most. The scans were done under manual control and the results were written down from the BM display. The order of the frequencies was differently randomised for each scan. The BM set-up was the same as above, apart from the fact that the 5 second time constant low-pass filter was used where noise fluctuations were a problem, and that scans were done in high and low cell constant modes. Polarisation controls were done by adjusting the 0.2 MHz conductance of distilled water using solid KCl, so that it had the same 0.2 MHz conductance as the relevant yeast suspension (see the Introduction for details).

The cell constants of the three probes were estimated using 10 mM KCl solutions of known temperature (i.e. known conductivity) at 1 MHz. With the BM set to high cell constant mode, all the probes had a cell constant of 1.24 cm$^{-1}$; in low mode the mAu probe's cell constant was 0.71 cm$^{-1}$.

The electrolytic cleaning system of the BM was never used during the preparation of the electrodes nor during the experiments unless otherwise stated. In experiments where they were used, the pulses were manually applied 10 times in succession, with the full cleaning cycle completed before the next pulse was activated. After the final pulse any gas bubbles adhering to the probes were shaken off and the capacitance and conductance signals at 0.2 MHz allowed to stabilise before the probes were scanned.

The experiments were carried out in a 600 ml glass beaker containing 500 ml of the relevant solution or suspension. The BM probe was situated with its tip central in the volume of liquid, so that the electric field it produced did not couple into the glass or flea used. The liquid was stirred at a constant 300 rpm and periodic checks were made to ensure that the electrode pins were free from air bubbles. The BM head-amplifier earth was clipped to the metal top of the stirrer.

Initial analysis of the capacitance spectra

Figure 3A:
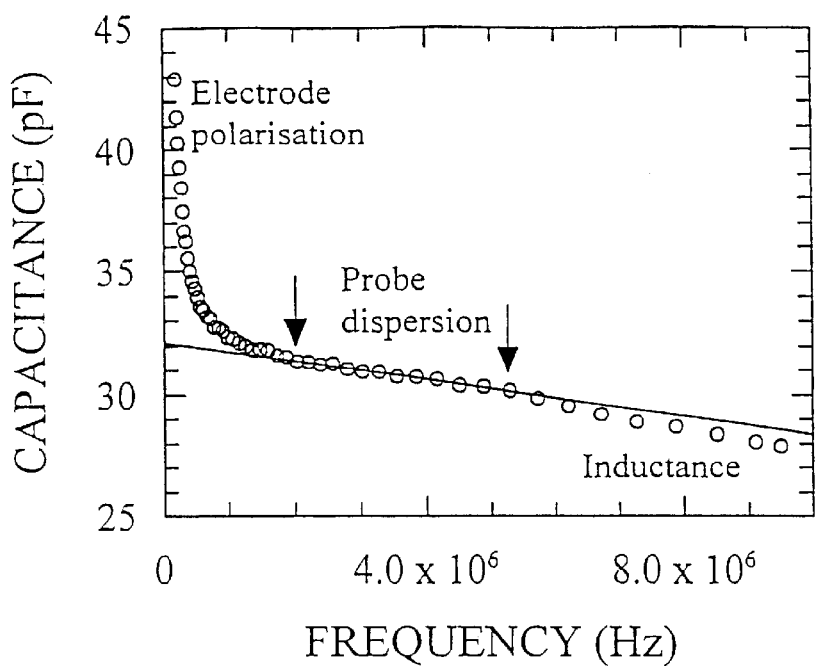
FIG. 3a is a graph illustrating the capacitance (dielectric) spectrum 56 mM aqueous KCl showing the fitted straight line used to eliminate the influence of the probe dispersion.
Figure 3B:
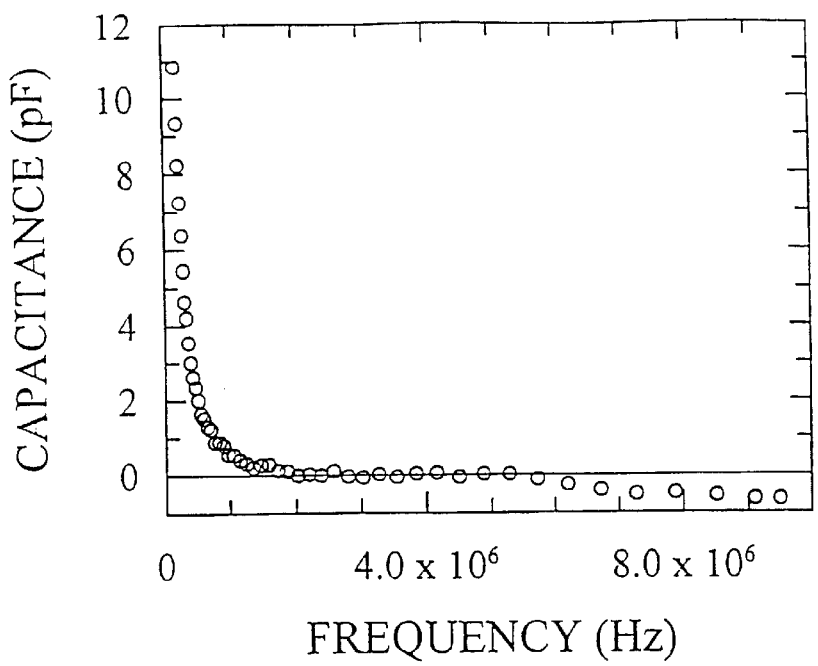
FIG. 3b is a graph illustrating the data from FIG. 3a after the subtraction of the straight line shown on that Figure.

To extract the electrode polarisation data from the frequency scans, the data had to be compensated for the distortions present in the capacitive spectra. The methods used to do this are illustrated in FIG. 3A which shows a frequency scan for 56 mM KCl (circles) measured in high cell constant mode under computer control. The electrode polarisation data are confined to the frequency range below about 1 MHz. The epoxy material making up the probe shaft itself disperses in the frequency range of interest and distorts the polarisation curve. Previous experiments have shown that this dispersion is essentially linear in the frequency range of the BM. Compensation for it can therefore be achieved by fitting a straight line to the capacitance data in the frequency range above the polarisation but below frequencies at which inductances distort the data at higher frequencies. The data used to get this linear fit are shown between the arrows on FIG. 3A and the fit to these data is the straight line shown. By subtracting this line from the frequency scan, not only removes the probe dispersion but also subtracts the offset under the polarisation curve due to the probe construction and the water in the solution used. FIG. 3B shows the data in FIG. 3A after this has been done and these types of probe compensated data are the basis of all subsequent analyses set out in this specification.

Results and Discussion

Effect of medium conductance on electrode polarisation

The object of the experiments was to create models that could be used to quantify electrode polarisation and then to use these as a means to develop techniques that could be used to remove the contribution of electrode polarisation to the capacitance spectra of biological cells. This would allow better biomass estimation and the generation of better quality dielectric spectra.

The first step in such an approach would be to fit the electrode polarisation to a mathematical function (such as a power or exponential functions) that describes the frequency dependence of the polarisation in terms of parameters that quantify the magnitude of the polarisation and how fast it falls with increasing frequency. The more these parameters could be made intuitive to BM users, the more useful they would be. Thus the first step required was to find a suitable mathematical function that describes the electrode polarisation over a wide range of polarisation magnitudes. The easiest way to generate the required data was to change the conductance of the medium being used.

Computer controller frequency scans were made using the mAu probe on aqueous KCl solutions that covered the entire conductance range of the BM (in high cell constant mode). Nineteen evenly spaced KCl concentrations were used starting at 10 mM and ending with 175 mM. To ensure that the experiment showed up any day-to-day variations in the response of the electrodes, the experiment was split into three parts. The second part was four days after the first and third part a further two days later. In-between days the probe was stored dry as described in the Methods section.

Table 1 shows in detail how the KCl concentrations were distributed across the three parts of the experiment and the random order the solutions were used in on each day. The random ordering was used to highlight and eliminate any memory effects that the electrode surfaces may have for previously used solutions. This complemented the random order of the frequencies in each scan as described in the Methods section. The 175 mM KCl concentration was likely to give the largest polarisation and to be most sensitive to day-to-day variations in the electrodes and was thus used as an inter- and intra-experiment part control. The fact that it was thought that chemometric or artificial neural network models of the polarisation might be necessary dictated that the whole KCl range was covered on each day. Not only would such models include the day-to-day variation, but parts 1 and 2 could be used to produce a model which could be checked by predicting the part 3 data etc.

FIGS. 3A and B show the results for 56 mM KCl. All the spectra from the experiment were converted to their probe compensated form as shown in FIG. 3B, using the procedure described in the Methods section. To model the resulting polarisation curves, it was necessary to separate the polarisation data below 1 MHz from the residual inductances that are present above 6 MHz (see FIG. 3B). At the same time, it was necessary to characterise the polarisation curves in a succinct and unambiguous form.

The shape of the capacitance curve below 1 MHz on FIG. 3B suggests two possible models, a power law model and an exponential model. The power law has the form:

$$^fC_p = {}^{1Hz}C_p f^p \tag{1}$$

where $^{1Hz}C_p$ is the capacitance due to polarisation at 1 Hz, f is the applied frequency (in Hz), p is the power term (dimensionless) and $^fC_p$ is the frequency dependent polarisation capacitance (in pF). $^{1Hz}C_p$ is used as a designation as it emphasises the fact that functionally Equation (1) acts as a constant capacitance (the capacitance at 1 Hz) scaled by the variable $f^p$ term. Linearised, Equation (1) becomes:

$$\log(^fC_p) = \log(^{1Hz}C_p) + p \log(f) \tag{2}$$

The exponential model is given by Equation (3):

$$^fC_p = {}^{0Hz}C_p e^{kf} \tag{3}$$

where k is the decay constant and $^{0Hz}C_p$ is the polarisation capacitance at 0 Hz (in pF). When linearised this becomes Equation (4):

$$\ln(^fC_p) = \ln(^{0Hz}C_p) + k f \tag{4}$$

Figure 4:
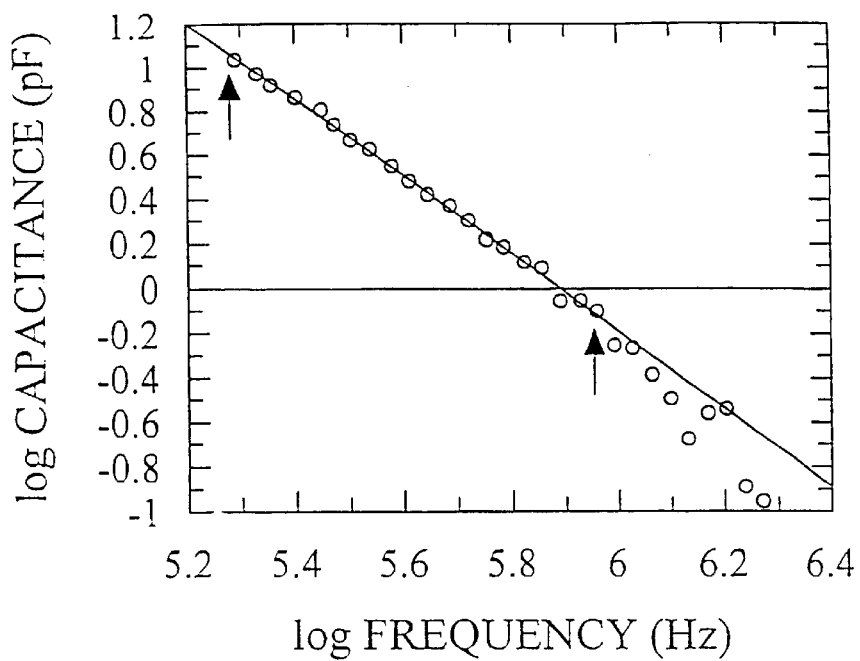
FIG. 4 is a graph illustrating the data from FIG. 3b plotted using the linearized power law and showing the linear fit to the data.
Figure 5:
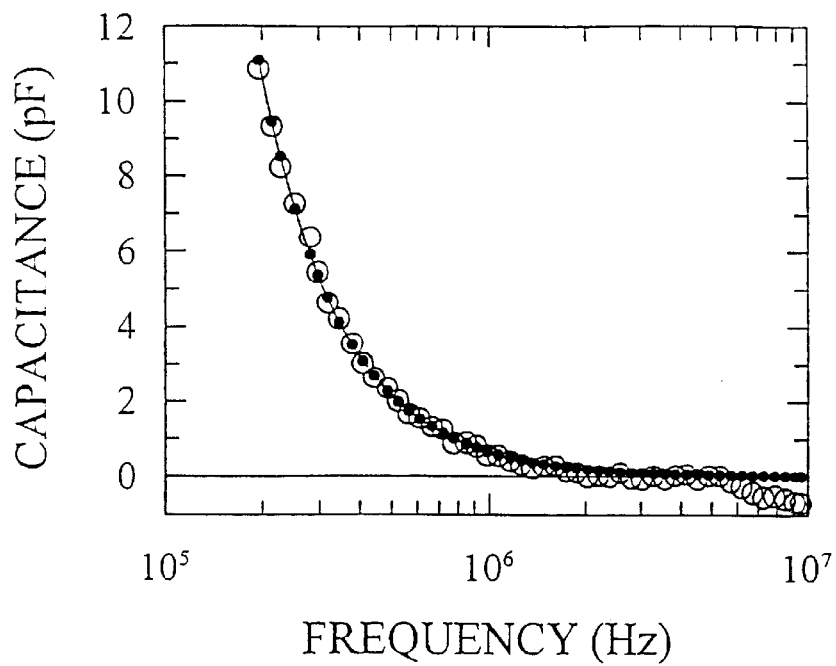
FIG. 5 is a graph illustrating the data from FIG. 3b plotted with the best fit to the power law derived from the straight line shown in FIG. 4.

Equations (2) and (4) were used to test the models on the probe compensated data like those shown on FIG. 3B. To do this the data at frequencies above where the capacitance first becomes zero or negative were discarded. FIG. 4 shows the data on FIG. 3B plotted in the form of Equation (2). The data between the arrows was used to produce the straight line fit shown. As can be seen a very good straight line is achieved at frequencies below about 1 MHz where the electrode polarisation dominates the capacitance spectrum. Thus the power law model provides an excellent way of characterising polarisation curves and indeed this is in line with previous studies. The line's y-axis intercept is $\log(^{1Hz}C_p)$ which gives a measure of the magnitude of the polarisation in $^{1Hz}C_p$. The line's slope is the power p which gives a measure of how rapidly the polarisation capacitance falls as frequency increases. Using these best fit $^{1Hz}C_p$ and p values in Equation (1) allows the polarisation data to be plotted as a function of frequency. This is done for the fit on FIG. 4 in FIG. 5 where the data points (open circles) shown are the probe compensated data from FIG. 3B. Once again the power law (dots and lines) provides a very good fit to the data.

A plot of the data on FIG. 3B using the linearised form of the exponential function (Equation (4)) failed to produce a straight line, indicating that electrode polarisation does not follow an exponential law.

Figure 6:
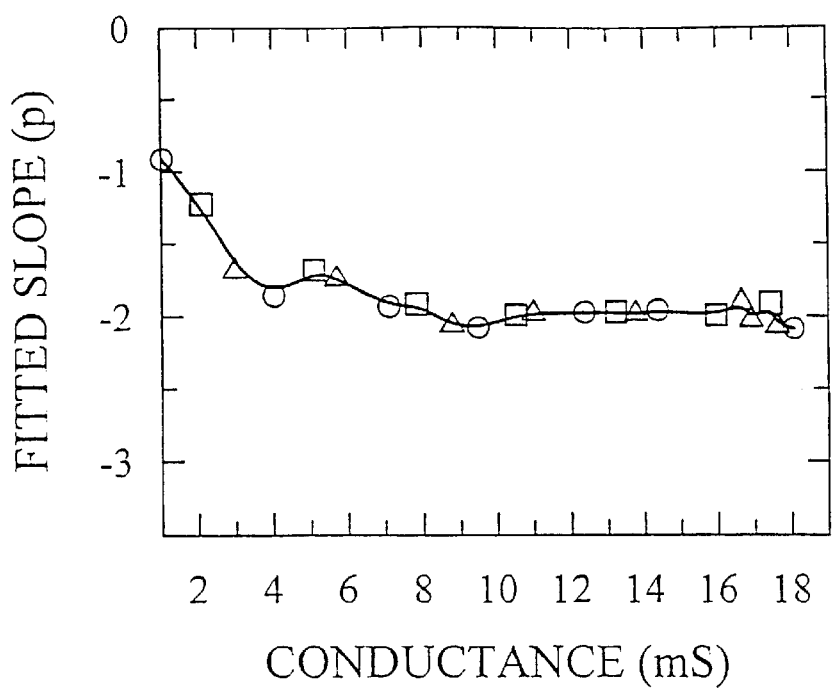
FIG. 6 is a graph illustrating the power law p value as a function of t conductance of aqueous KCl.

All the frequency scans from this experiment were analysed using the power law model to give p and $^{1Hz}C_p$ values. In all cases the power law provided an excellent fit to the data. FIG. 6 is a plot of the fitted p values versus the conductance of the KCl solutions at 1 MHz for the three parts of the experiment. The circles are part one of the experiment, the squares part two and the triangles part three (see Table 1). The interpolated line is a 4 spline to all the data. A full discussion of this plot will be provided later in the context of the half frequency ($^hf$) which is derived directly from it but is far more intuitive to use. It will suffice to note that above about 7 mS the p value is a constant of about—2(mean=−1.99,S.D.=0.060) which puts Equation (1) into the form of an inverse square law: $^fC_p = {}^{1Hz}C_p(1/f^2)$.

Figure 7:
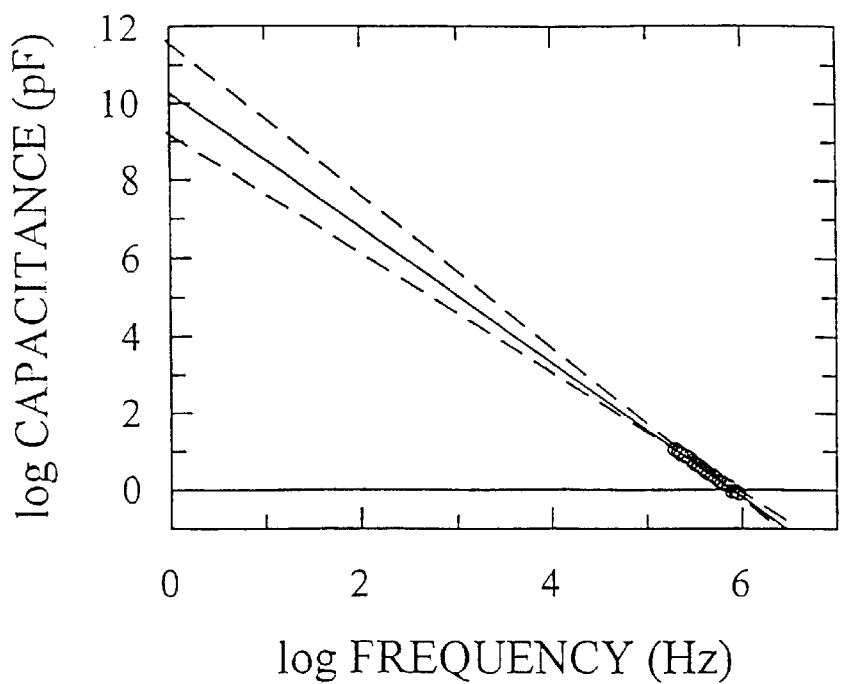
FIG. 7 is a graph illustrating he potential errors in characterizing the magnitude of electrode polarization by $C_p$.

There is a problem with using $^{1Hz}C_p$ as a measure of the magnitude of the electrode polarisation. On FIG. 4 there is a little noise on the data which means that another scan of the same solution might produce a slightly different fitted line. Within the BM's frequency window (see FIG. 4) the line would not be significantly different, but extrapolated back to the 1 Hz required to get $^{1Hz}C_p$ these differences could become quite large. This would produce large artefactual differences in the magnitude of polarisation where in fact, in the range where data were taken, there were no significant differences. Just how large these extrapolations are is illustrated by FIG. 7 which shows the linear fit on FIG. 4 (solid line) extrapolated back to 1 Hz, along with the data values (open circles) used for the fitting (between the arrows on FIG. 4). The two dotted lines show how plausible fits to the data could, when extrapolated over such a large frequency range, give very different estimates of the magnitude of the polarisation (as measured by $^{1Hz}C_p$). Note that a log y-axis is used and so even minor differences in the y-intercept values could give very large differences in the estimated $^{1Hz}C_p$ values derived from them.

To make the characterisation of the electrode polarisation curves using the power law model more reliable, a measure is needed of the magnitude of the polarisation that characterises it in the frequency range where we actually have data. At the same time a more intuitive form of p, the measure of the how steep is the fall in capacitance with increasing frequency, would be useful. Ideally this should enable a consideration of an actual set of BM polarisation data (such as FIG. 3A or B) to see straight away how the measure relates to them. This would not only make searching for trends in the data far easier but it would enable BM users to monitor the polarisations they are getting with their electrodes quickly and routinely.

Figure 8:
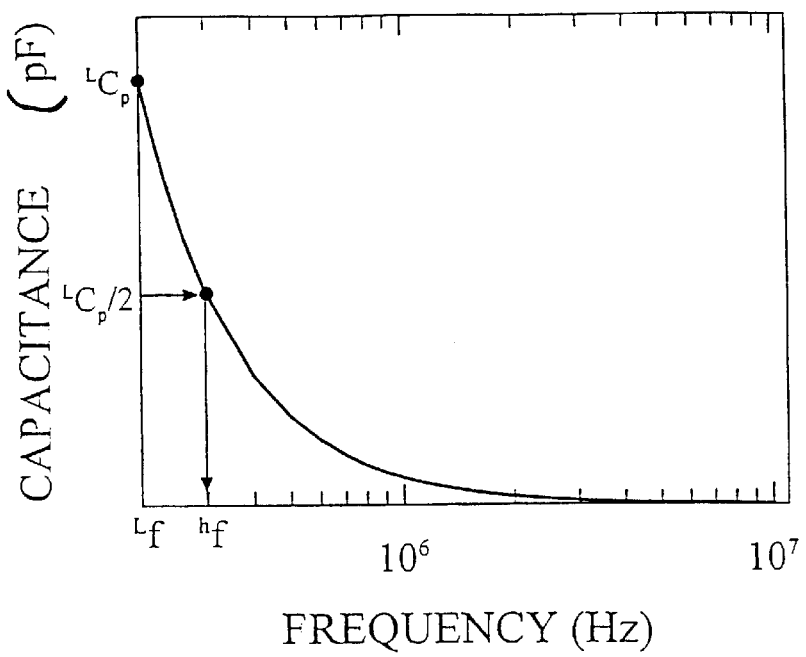
FIG. 8 is a graph characterizing electrode polarization using $^L f$, $^h f$ and $^L C_p$.

The logical measure of the magnitude of the polarisation in the BM's frequency range is to quote it as the extent of the polarisation at the lowest frequency used. The lowest frequency is called $^L f$ (in Hz) and the polarisation capacitance at it, $^L C_p$ (in pF). As a power law is being used to model the polarisation, one does not have a half-life to characterise the rate of fall of capacitance with increasing frequency but by analogy use could be made of the frequency when the capacitance at $^L f$ (i.e. $^L C_p$) has halved: this is called the half-frequency ($^h f$). FIG. 8 is an illustration of how $^L f$, $^L C_p$ and $^h f$ relate to a set of probe compensated data in the BM's frequency range. Note that both $^L C_p$ and $^h f$ only have meaning when quoted in conjuction with their equivalent $^L f$ and that both terms refer to the polarisation only.

For very rough and ready routine monitoring of electrode polarisation, use could be made of a high conductance solution where the polarisation swamps any baseline slope. An estimate of $^L C_p$ could then be made as the difference in capacitance between an $^L f$ of 0.2 MHz and the end of significant polarisation at about 2 MHz. An estimate of lf could then be made by setting the BM to 2 MHz and dialling the frequency back towards 0.2 MHz until the capacitance had risen by half this difference.

For detailed studies of polarisation, it is necessary to relate $^L C_p$ and $^h f$ to the fit of the power law model to real BM data as illustrated on FIG. 4. To do this, it is necessary to convert the $^{1Hz} C_p$ and p values such a fit gives directly to $^L C_p$ and $^h f$. To get $^L C_p$ (in pF) the lowest frequency ($^L f$, in Hz) is selected, which for the BM is typically $2.10^5$ Hz, and inserted along with the best fit $^{1Hz} C_p$ (in pF) and p values, into Equation (1) and then $^L C_p$ is calculated directly. The derivation of $^h f$ from p is a little more complicated and is detailed in Appendix 1. The result of the derivation there is that p and $^h f$ (in Hz) are related by Equation (5):

$$^h f = {^L f} \, 2^{\frac{-1}{p}} \quad (5)$$

Figure 9:
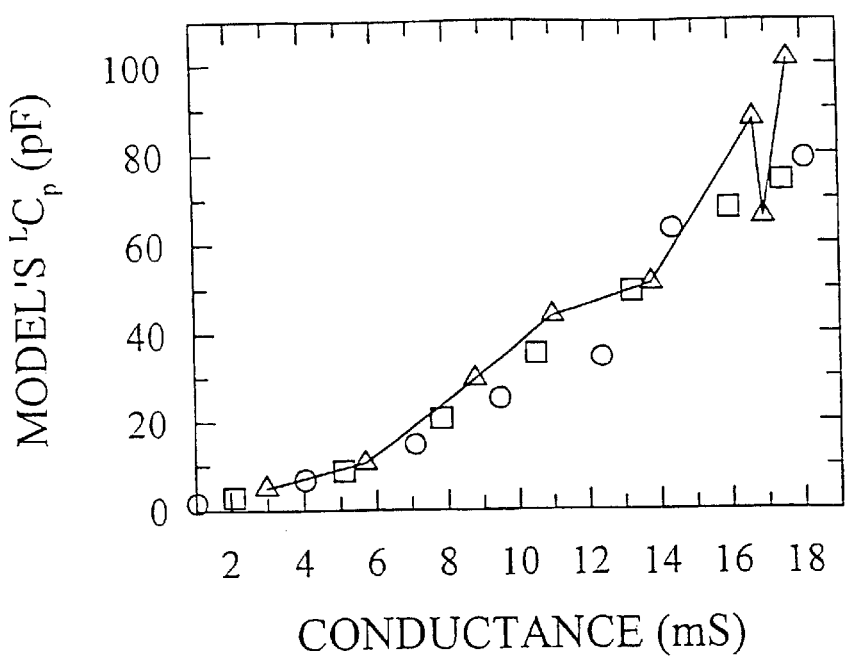
FIG. 9 is a graph illustrating the magnitude of the electrode polarization, as expressed by $^L C_p$, as a function of the conductance of aqueous KCl.

The p and $^{1Hz} C_p$ values for all the KCl solutions were converted to their equivalent $^h f$ and $^L C_p$ values using the BM's lowest frequency of $2.10^5$ Hz as $^L f$. FIG. 9 is a plot of the $^L C_p$ values versus the 1 MHz conductance of the KCl solutions, over the three parts of the experiment (see Table 1). The circles are for part one, the squares part two and the triangles and line are for part three. As expected there is a general increase in the magnitude of the polarisation as the solution conductance increases. There is however significant day-to-day variation and some large changes even within one part of the experiment.

Figure 10:
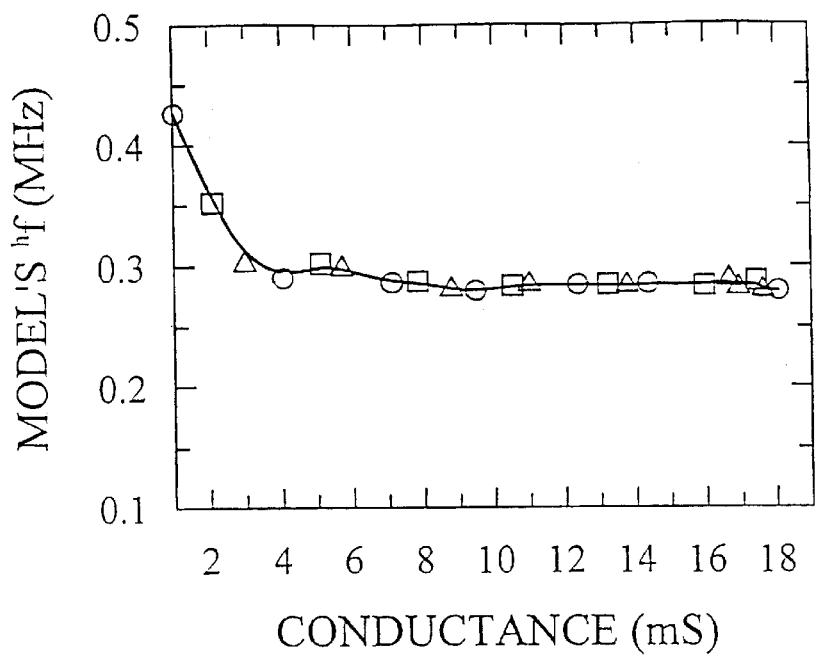
FIG. 10 is a graph of the $^h f$ of electrode polarization as a function of the conductance of aqueous KCl.

FIG. 10 is a plot of the $^h f$ values versus the 1 MHz conductance of the KCl solutions, over the three parts of the experiment (see Table 1). The circles are for part one, the squares part two and the triangles part three. The line through the data is a 5 spline. Importantly, there is virtually no inter- or intra-experimental variation in these values. Above about 3–7 mS the $^h f$ is almost constant at about 0.28 MHz (relative to the $^L f$ of 0.2 MHz). This is quite remarkable given the wide variations in the magnitude of the polarisation over this conductance range. Also the BM's electronics are configured to increase the current density across the electrode interfaces as the conductance increases which will itself alter the polarisation. The tip-up in $^h f$ at lower conductances is not due to polarisation but reflects a baseline anomaly of the BM itself which becomes evident only at low conductances. From FIG. 9 it can be seen that these elevated $^h f$ values correspond to small "polarisation" magnitudes.

Using the constant $^h f$ value at conductances greater than 7 mS to reduce electrode polarisation by the use of a 2 frequency (2f) method.

So far it has been shown that electrode polarisation can be modeled by a power law and that the parameters of this model can be simply modified to give reliable and intuitive measures of magnitude ($^L C_p$) and rate of fall of polarisation with increasing frequency ($^h f$). It was further shown that above a certain value of conductance (3–7 mS) the $^h f$ was constant.

Figure 11:
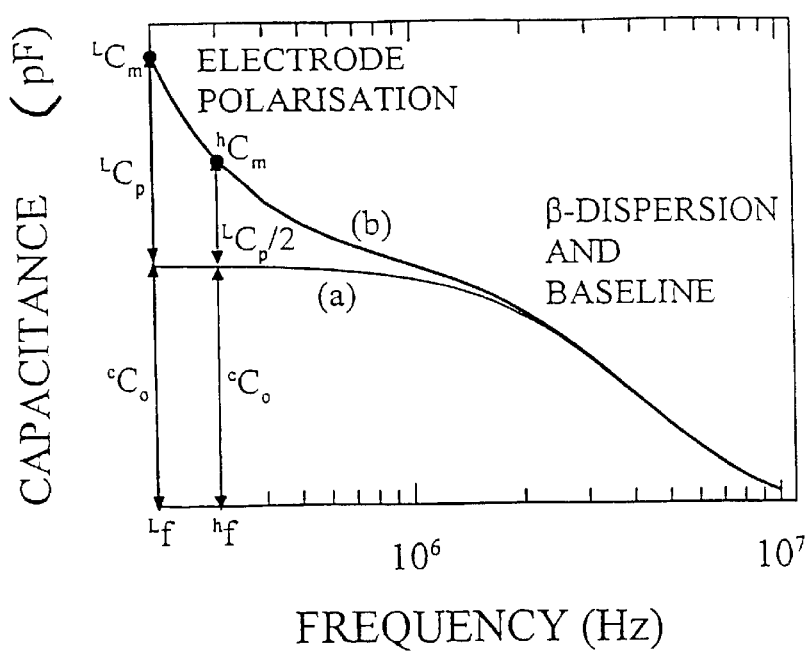
FIG. 11 is a graph of the use of measurements at $^L f$ and $^h f$ to eliminate electrode polarization from the capacitance spectrum of a suspension of biological cells.

A most useful consequence of this constant $^h f$ (the value of which may vary from BM to BM) is that it can be exploited to eliminate electrode polarisation from biological capacitance spectra rather directly, without the need, for example, to use artificial neural network or chemometric models. The principle of this method is illustrated in FIG. 11. What is shown is the β-dispersion (on its instrumental baseline) which it is sought to measure (line (a)), along with the same dispersion embedded in electrode polarisation as might be measured in reality (line (b)). What one would like to do is take some spot capacitance readings and use these to estimate the way the polarisation falls with frequency. Having done this, the calculated polarisation curve would be subtracted from the measured capacitance spectrum (line (b)) to leave the underlying β-dispersion (plus baseline) uncontaminated by polarisation (line (a)). For most of the β-dispersions one would wish to study or use to quantify the biomass concentration, the values of $f_c$ are such that one is largely on the low-frequency plateau by the time the frequency falls below about 0.3 MHz (see later for a detailed discussion of this). Under these conditions, a spot capacitance measurement can be taken at $^L f$ (typically $2.10^5$ Hz). This measured capacitance is called $^L C_m$ and from FIG. (11) it is given by:

$$^L C_m = {^c C_o} + {^L C_p} \quad (6)$$

where $^c C_o$ is the capacitance offset under the polarisation curve (in pF) which is made-up of the β-dispersion plateau and the equipment baseline. If another spot capacitance measurement is taken at the half frequency to give $^h C_m$ (in pF) we see from FIG. 11 that this is given by:

$$^h C_m = {^c C_o} + \frac{^L C_p}{2} \quad (7)$$

where $^c C_o$ is the same as before. This pair of simultaneous equations is easily solved by subtracting Equation (7) from Equation (6) to give Equation (8).

$$^L C_p = 2({^L C_m} - {^h C_m}) \quad (8)$$

For this method the offset is taken as any capacitance that the polarisation curve sits on and is usually made-up of the β-dispersion curve and the instrument's (BM's) baseline. Note that for all of this document a constant offset refers to the fact that the offset is identifal at $^L f$ and $^h f$, at other frequencies the offset will differ as the cell dispersion occurs and the BM baseline changes.

As $^L f$ is selected and $^h f$ is a known constant, spot measurements of the capacitance of the suspension can be taken at these frequencies (to give $^LC_m$ and $^hC_m$ respectively). Equation (8) then gives the magnitude of the electrode polarisation at $^Lf$, i.e. $^LC_p$ (see FIG. 8). To calculate how this polarisation capacitance falls as frequency increases, it is necessary to use the measures of the rate of fall of capacitance with increasing frequency, namely p or $^hf$. As we have consistently been using $^hf$, and as its use only slightly increases the complexity of the algebra, the equation describing the fall in polarisation capacitance in the BM's frequency range was derived for this. Appendix 2 describes the derivation of Equation (9) which describes the fall in polarisation capacitance in terms of the applied frequency f, $^Lf$, $^hf$ (all in HZ) and $^LC_p$ (in pF).

$$^fC_p = {}^LC_p 2^{(\log(Lf/f)/\log(hf/Lf))} \qquad (9)$$

Thus having obtained $^LC_p$ from Equation (8), f in Equation (9) can be varied to generate the electrode polarisation curve. This curve can then be subtracted from the full biological spectrum (line (b) in FIG. 11) to give the polarisation-free β-dispersion on its BM baseline (line (a) in FIG. 11).

Effects on polarisation of factors that might be encountered in fermentations.

For the 2f method to be a useful way of eliminating electrode polarisation in practical situations, the $^hf$ must not change significantly when the electrodes are exposed to the environmental changes that are likely to occur during fermentations. In addition, it is necessary to quantify the effect of changing the probe on the if as this will dictate whether an instrument would need to be recalibrated for each probe if the 2f method was implemented in its hardware.

To investigate these possible influences, an experiment was carried out under computer control as described in the Methods section. The BM's electrolytic cleaning pulses were applied during this experiment. These pulses generate electrolysis bubbles at the pin's surfaces which dislodge any adhering fouling material, but also are known (and are designed) to alter the magnitude of the electrode polarisation. Thus the order in which each part of this experiment was done is very important and this dictates the order of the descriptions of these experiments below. In all cases the capacitance spectra fitted the power law model very well and the data were analysed to give $^hf$ and $^LC_p$ values relative to a $^Lf$ value of $2.10^5$ Hz.

Figure 12A:
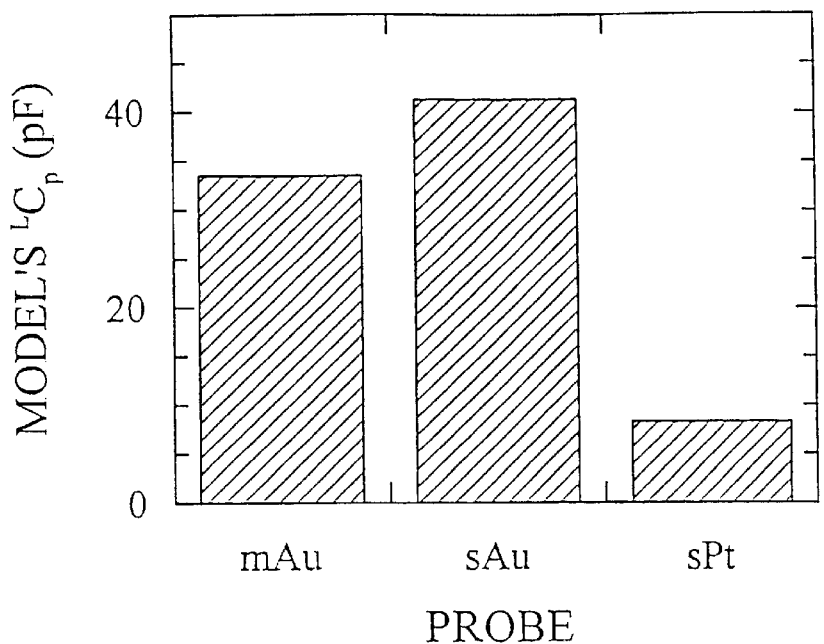
FIG. 12a is a graph illustrating the influence of using gold (Au) and Platinum (Pt) pinned electrodes on the $^L C_p$ of 120 mM aqueous KCl.
Figure 12B:
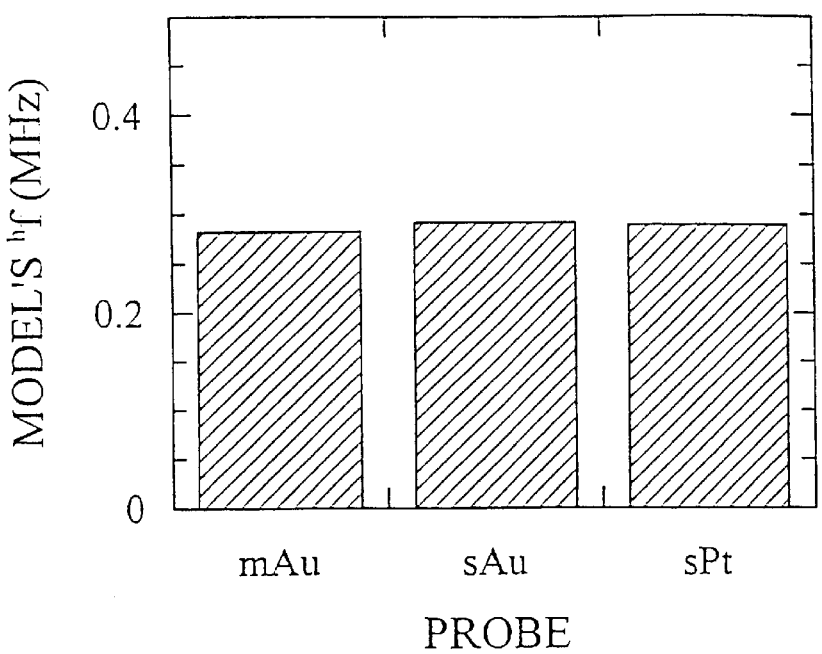
FIG. 12b is a graph illustrating the influence of using gold (Au) and Platinum (Pt) pinned electrodes on the $^h f$ of 120 mM aqueous KCl.

First, the effect of changing probes (and probe material) was investigated by scanning the mAu, sAu and sPt probes in 120 mM KCl. The order in which the probes were used was randomised. The results are shown in FIGS. 12A and B for $^LC_p$ and $^hf$ respectively. The probes were used in the order shown from left to right. From A it can be seen that there is quite a large variation in the magnitude of the polarisation even between gold probes. Whether the matt or smooth finish has any significant effect here cannot be ascertained from just the two probes used. Certainly roughing the surface of probe pins is a standard way of reducing their polarisability and indeed forms the rationale for blacking platinum-pin electrodes. The large reduction in polarisation magnitude on using platinum pins was expected, since this metal is known not to polarise as greatly as other metals. However the sPt probe, whilst giving very significant improvement over gold, still had sufficient polarisation to pose potential problems when measuring small biomass concentrations. However, FIG. 12B gives the $^hf$ values for the three probes, where it can be seen that although the polarisation $^LC_p$ values are very different, these $^hf$ values are all identical with the values in the KCl concentration experiment (which was in fact performed about one and a half months previously).

Figure 13A:
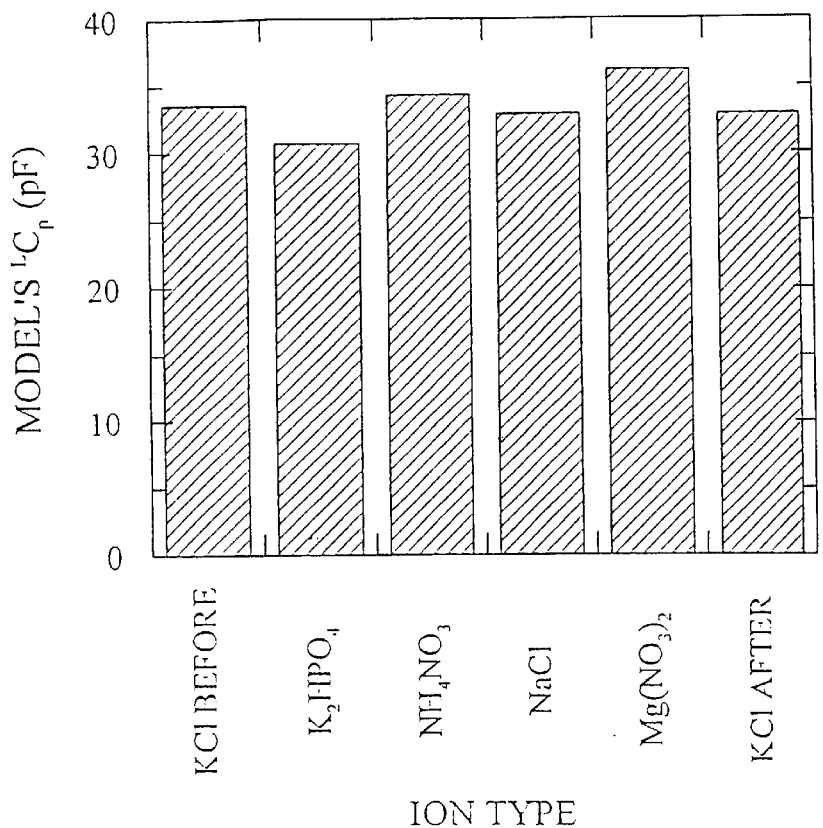
FIG. 13a is a graph illustrating the influence of ion sizes on $^L C_p$.
Figure 13B:
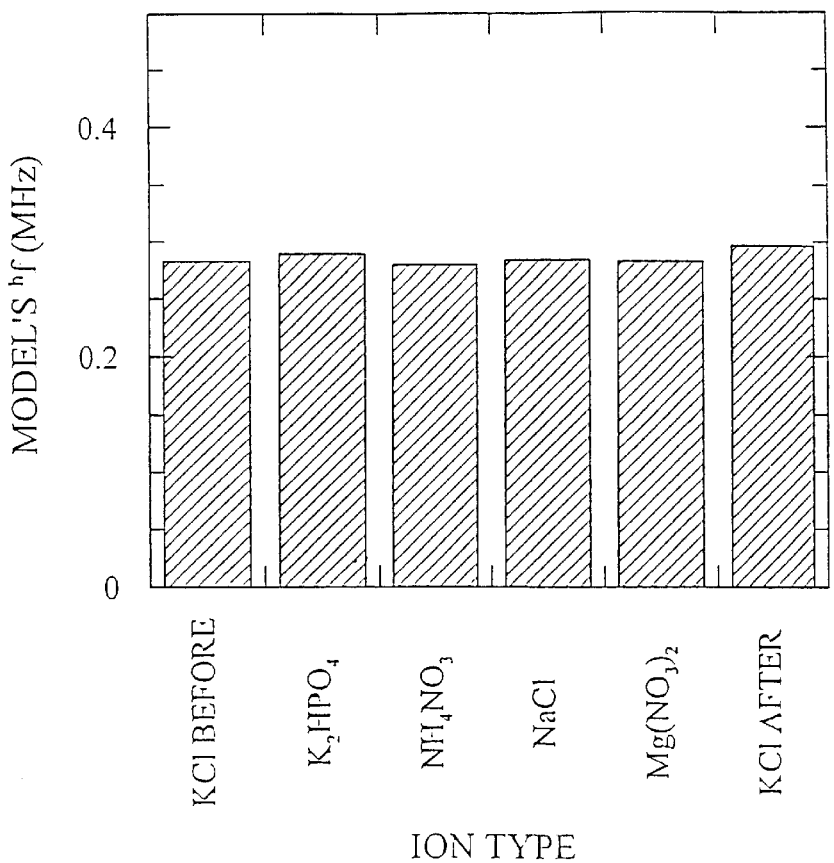
FIG. 13b is a graph illustrating the influence of ion sizes on $^h f$.

Next the mAu probe was exposed to solutions containing ions of different sizes as this would be expected to effect the polarisation by altering the Stern layer at the pin's surfaces. As controls, 120 mM KCl was scanned at the start and end of the experiment. The ionic solutions were adjusted using the relevant solid salt to have the same 1 MHz conductance as the KCl solution, as described in the Methods section. This means that the same current densities should be crossing the pin/aqueous interface in all cases. The order the salt solutions were scanned in was randomised and are shown in the order used (left to right) on FIG. 13. FIG. 13A shows that the $^LC_p$ values were again different for the various solutions, although none of these differences were particularly great. However, FIG. 13B again shows that even though the magnitudes of the polarisation may change the $^hf$ value is a constant.

Fouling of the electrodes has long been known to represent a potential source of the variations in the magnitude of electrode polarisation seen during fermentations. To investigate this the mAu probe was scanned in 120 mM KCl and then in a lysed yeast suspension with the same conductance as that of the KCl solution (see the Methods section for details). FIGS. 14A and B shows the $^LC_p$ and $^hf$ results, which once again shows that the $^hf$ is maintained at the value seen in all the previous experiments (given a sufficient conductance).

During many fermentations, it is likely that the BM's electrolytic cleaning pulses will be applied to the electrodes to remove any fouling that may have occurred. To test the effect of this, the three probes were electrolytically cleaned in 120 mM KCl as described in the Methods section. Immediately before the cleaning, a control scan in 120 mM KCl was done (pre-pulses scan). The order of the probes in this experiment was randomised and are shown in the order used (left to right) on FIG. 15. FIG. 15A shows the pre- and post-cleaning pulse $^LC_p$s for each probe. For each of the probes the cleaning resulted in a drastic reduction in the magnitude of the polarisation, in line with previous observations. The reason for this reduction is probably that the cleaning both removes material adhering to the probes and removes some of the metal, revealing a fresh uncontaminated surface. The problem with using the cleaning pulses to reduce polarisation during fermentations is that after the cleaning the polarisation can start to increase again and this can make the biomass concentration measured at a spot frequency appear to fall and rise after cleaning is applied. Excessive use of the cleaning can result in metal being put into solution and even routine use of the pulses can result in the probe pins getting a matt finish or being covered in material precipitated out of the fermentation broth. In spite of all of this, FIG. 15B again demonstrates that the $^hf$ is a constant value under these conditions.

The last part of the experiment again involved the mAu probe only. This time the probe was scanned in 120 mM KCl, then scanned in the lysed yeast, then cleaning pulses applied whilst in the yeast, and finally rescanned in the yeast. FIG. 16A shows that the decrease in $^LC_p$ caused by the previous set of cleaning cycles was carried over to this part of the experiment. The application of additional cleaning did not reduce the polarisation magnitude any further. FIG. 16B shows that the treatments had little if any affect on the probe's $^hf$. It thus seems that the $^hf$ is a constant, although of course different instruments may have different values for this constant.

Simulations and modelling of the effect of a sloping offset under the polarisation on the 2f method for removing electrode polarisation.

The two sets of experiments described above showed that the $^hf$ for the electrode polarisation was independent of medium conductance (above a few mS), electrode metal, which probe was used, the ions in the medium, electrode interface current density, the presence of fouling materials, and electrolytic cleaning pulses. These results mean that the 2f procedure to eliminate polarisation could be used for real fermentations.

Figure 1:
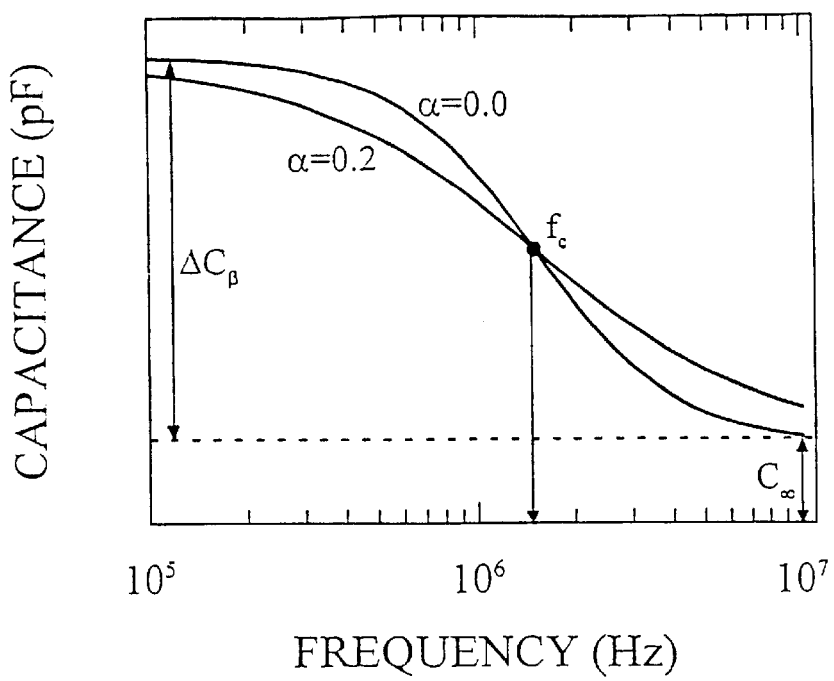
FIG. 1 is a graph illustrating the β-dispersion of a suspension of biological cells illustrating the influence of an α value greater than zero.
Figure 2:
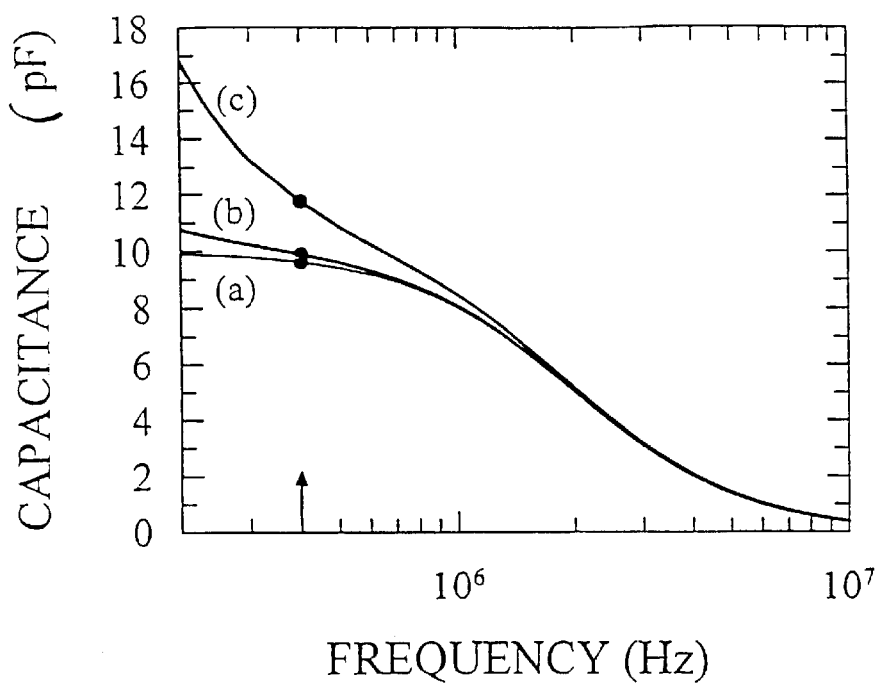
FIG. 2 is a graph illustrating the influence of electrode polarization on single and dual frequency biomass measurements.

The major limiting assumption underlying the 2f method is that it assumes the capacitance offset ($^cC_o$) under the polarisation curve is the same at $^Lf$ and $^hf$ (see FIG. 11). This may not be true within the BM's frequency range and especially if $^Lf$ and $^hf$ values of 0.2 and 0.28 MHz respectively are used. A β-dispersion with a low $f_c$ and a significant Cole-Cole α value (e.g. animal cells) may not fully reach the low-frequency plateau in the BM's frequency range (see FIG. 1). FIG. 3A showed that the BM's baseline itself may slope in the frequency range of interest.

FIG. 17 illustrates the effect that a sloping offset would have on the 2f model. Line (a) is a capacitance scan of a cell suspension contaminated by electrode polarisation. Line (b) is the offset under this polarisation and comprises the β-dispersion and any instrumental baseline effects. As can be seen, this offset drops significantly between the $^Lf$ and $^hf$ shown on the plot. If spot measurements of the suspension capacitance were taken at $^Lf$ and $^hf$ (to give $^LC_{m.\Delta o}$ and $^hC_{m.\Delta o}$, the Δo indicates that the offset changes between $^Lf$ and $^hf$) and the 2f model used to back-calculate the frequency dependence of the polarisation the true polarisation curve (line (d)) is not obtained. In fact, an over-estimation is obtained of the polarisation (line (e)), which when subtracted from the suspension spectrum (line (a)) does not give the true offset (line (b)) but a slightly distorted version (line (c)). This slight distortion does not cause a significant problem for biomass estimation if use is made of a biomass measuring frequency (upward pointing arrow) slightly above the $^hf$ used, as illustrated on the Figure. The downward pointing arrow highlights the significant reduction in the polarisation at the measuring frequency that the application of the 2f method has effected.

To investigate the effect that a non-constant offset might have on biomass measurements under realistic but controlled conditions, simulations were performed. For the simulations the $^Lf$ used was $2.10^5$ Hz. As the simulations would be based on the results gained for the mAu probes, the $^hf$ used would be taken from its data. The mAu $^hf$ values for all the scans where the conductance was >=7 mS were used from the two experiments described above. The mean (to the number of decimal places the BM offers) was 0.28 MHz (S.D=0.0061 MHz) and this was used as the $^hf$ for all the simulations. The use of an averaged $^hf$ would show-up any effects on the 2f method caused by real but slight differences in $^hf$. The chosen biomass measuring frequency was 0.4 MHz as this is typical of real biomass measurements. A set of simulations was generated using the data from the KCl concentration experiment earlier, by carrying out the following at each concentration.

(1) A set of simulation cell suspension data with a sloping offset was generated. For each KCl concentration two such sets were generated, each using β-dispersions with different $f_c$ values, as follows.

(a) To obtain a realistic BM baseline under the polarisation curve the actual straight line fitted to the probe dispersion at that concentration was used. Thus for the simulation equivalent to the 56 mM KCl data the straight line on FIG. 3A was used. In a real biomass measurement the capacitance of the un-inoculated medium would be zeroed prior to the experiment. To simulate this the straight line was offset so that it crossed the abscissa at 0.4 MHz.

(b) Next β-dispersion data were simulated and added to the baseline generated in (a) to give the offset curve under the polarisation. At each KCl concentration the same pair of simulated β-dispersions were used to produce the simulated data sets needed. The dispersions were generated using the Cole-Cole equation using $\Delta C_\beta=20$ pF, $\alpha=0.15$ and $C_\infty=0$ and two different $f_c$ values. The lower $f_c$ value was 0.75 MHz and gave a realistic dispersion for large cells like animal cells. This low $f_c$ in combination with the large α value caused the dispersion to be significantly off the low-frequency plateau region over the frequency range of the BM simulated here (see FIG. 1). The second dispersion had a higher $f_c$ of 1.5 MHz which is typical of yeast cells.

(c) The polarization curve used was the power law fitted to the real data at the KCl concentration of interest. Thus for the 56 mM KCl simulation the $^{1Hz}C_p$ and p values from the fitted line on FIG. 4 were put into Equation (1) to generate the polarisation curve. This polarisation curve was then added to the two sets of offset data generated in (b) to give the required pair of simulated cell suspension date.

FIG. 18A shows the BM baseline data (closed circles), β-dispersion (fc=0.75 MHz) (squares) and polarisation data (open circles) equivalent to 175 mM KCl generated as above. FIG. 18B shows the resulting offset data (closed circles, equals BM baseline+β-dispersion) and simulated (test) suspension data resulting from the plots in A (open circles, equals BM baseline+β-dispersion+polarisation). Note how embedded the offset data (including the β-dispersion) are in the polarisation.

(2) Once the test suspension data had been generated (1 set for each fc at each KCl concentration) each was then used to test the 2f method. The capacitance values at the fixed $^Lf$ and $^hf$ were taken and inserted into Equation (8) to give the 2f method's estimate of $^LC_p$. This value was then inserted into Equation (9) to generate an estimate of the frequency dependence of the polarisation ($^fC_p$) which was then subtracted from the cell suspension data to give an estimate of the underlying offset curve free from polarisation. FIG. 18C shows the simulated cell suspension data (open circles) from B along with the correct offset (line) and the 2f method's estimate of this offset generated as above (squares). It is seen that the estimated offset dips slightly below the real value at low frequencies but by the measuring frequency of 0.4 MHz it is very close to the true value. The arrow indicates just how much polarisation had been removed by the application of the 2f method to biomass estimation at 0.4 MHz. It should be noted that at 0.4 MHz the offset component due to the baseline of the BM is zero and so the offset capacitance is due entirely to the β-dispersion.

FIG. 19 summarises the repeating of the simulation in FIG. 18 over a wide range of conductances (plotted as their 1 MHz values) using the low-frequency β-dispersion fc (A) and the high frequency fc (B). On each plot are shown the simulated cell suspension capacitance values at the measuring frequency of 0.4 MHz (circles), along with the correct offset (in this case β-dispersion) value at that frequency (line). The application of the 2f method to the simulated suspension data resulted in the estimates of the 0.4 MHz offset capacitances which are dotted along the correct value line (squares). The 2f model thus seems to work for all the conductances above 7 mS. At the high conductances it accurately reveals the β-dispersion even though it is completely embedded in the polarisation data. At the other conductance extreme it effectively removes the polarisation even though the slope in the offset is significant compared to the magnitude of the polarisation present.

The reason the 2f method could not be applied to conductances below a few mS was that below this threshold the $^4$f became conductance dependent due to instrumental artifacts (see FIG. 10). It is entirely possible that these low conductance $^h$f values are stable and so a calibration curve such as that in FIG. 10 could be used to read off the $^h$f values to use in the 2f method at these low conductance values.

Follow-up simulations were done to investigate the effects of noise spikes disturbing one or other of $^L$f and $^h$f during frequency scanning. These were done exactly as above but only on the 120 mM KCl data (as this is in the mid-conductance range) and with the higher $f_c$ β-dispersion. After the simulated cell suspension data were generated, the capacitances at $^L$f or $^h$f were altered before being fed into the 2f method. The estimated offset capacitances after using the 2f method to remove the polarisation were then compared to the real values as before. The following alterations were each given their own simulation, $^L C_m$+0.5 pF; $^L C_m$−0.5 pF; $^h C_m$+0.5 pF; $^h C_m$−0.5 pF; $^L C_m$×0.96, and $^h C_m$×0.96. In all cases the errors in the resulting estimated offset curves were small at the biomass measuring frequency of 0.4 MHz.

Values for $^L$f, $^h$f and the biomass measuring frequency of 0.2, 0.28 and 0.4 MHz respectively seem to work extremely well. If a BM was set-up to do just biomass measurements it would take spot cell suspension readings at these three frequencies only and estimate $^L C_p$ using Equation (8). It would then estimate the polarisation at 0.4 MHz ($^{0.4\ MHz}C_p = {^L C_p}\times 0.23981$, from Equation (9)). This $^{0.4MHz}C_p$ would then be subtracted from the capacitance actually measured at 0.4 MHz for the cell suspension to give the value corrected for polarisation. The procedure can easily be implemented on a PC.

As a difference in the capacitance offset under the polarisation curve was so pivotal to the use of the 2f method it was decided to model its effect on the method explicitly. Changes in the offset capacitance at $^L$f and $^h$f might be caused by the BM baseline sloping, the β-dispersion not being on its low frequency plateau, a noise spike affecting the capacitance data at one of the frequencies, or the tail-end of a lower frequency dispersion such as α-dispersion. The model of the error would thus be applicable to a wide range of situations. The derivation of the error function is described in detail in Appendix 3 but a brief description will be given here. The aim is to quantify the percentage error in the polarisation curve estimated using the 2f model when the offset changes between the $^L$f and $^h$f. FIG. 17 illustrates the effect of such an offset change on the polarisation estimated by the model. The correct polarisation curve is shown as line (d) which has the correct $^L$f magnitude, $^L C_p$. Because of the change in the offset, what the 2f model actually gives is line (e). The aim is to express the different between the polarisation lines (e) and (d) as a percentage of the correct values given by line (d). Thus obtained is a percentage error in the estimated polarisation as a function of frequency ($^f E_p$) which is given by:

$$^f E_p = \frac{^f C_p \text{ with offset error} - {^f C_p} \text{ without offset error}}{^f C_p \text{ without offset error}} \frac{100}{1} \quad (10)$$

On FIG. 11 the offset capacitance values were the same (namely $^c C_o$) at $^L$f and $^h$f. For the cases where the offset changes, one calls the off set at $^L$f, $^L C_o$ and the offset at $^h$f, $^h C_o$. The magnitude of the change in the offset capacitances is then defined as $\Delta C_o$ as given by:

$$\Delta C_o = {^h C_o} - {^L C_o} \quad (11)$$

The results of the derivation in Appendix 3 gives the values of $^f E_p$ as:

$$^f E_p = -2\left(\frac{\Delta C_o}{^L C_p}\right)\frac{100}{1} \quad (12)$$

Note that the percentage error in the estimated polarisation ($^f E_p$) is frequency-independent, thus the difference between lines (e) and (d) on FIG. 17 is always the same proportion of (d). The size of this percentage error is given by the ratio of the change in the offset between $^L$f and $^h$f (namely $\Delta C_o$), to the correct magnitude of the polarisation at $^L$f (namely $^L C_p$). Thus if $\Delta C_o$ is a hundredth of $^L C_p$ the two-frequency method produces a frequency independent 2% error in the calculated $^f C_p$ values. In addition offsets that slope down have negative $\Delta C_o$s and so cause an overestimation of the polarisation.

It is important to remember that polarisation curves such as line (e) on FIG. 17, which contain an error due to a non-constant offset, do not cause significant problems for biomass estimation. When line (e) is subtracted from the measured suspension data, line (c) is obtained rather then the correct line (b), but by the biomass measuring frequency the difference between the two lines is usually quite small (and hopefully small compared to the value of line (b) at that frequency).

Application of the 2f method of removing electrode polarisation to real yeast suspensions.

Suspensions of live yeast were made up and scanned on a BM in high and low cell constant modes using the mAu probe, as described in the Methods section. To access the shape of the polarisation curves, the polarisation control data were fitted to the power law and the $^h$f and $^L C_p$ (relative to an $^L$f of 0.2 MHz) calculated as before. The power law fits were very good in both high and low cell constant modes and yielded $^h$f values of 0.29 and 0.28 MHz receptively. Thus even though this experiment was done some five months after the previously described one, the $^h$f had not changed. In addition the $^h$f values were the same irrespective of which cell constant modes were used.

FIGS. 20A and B show the frequency scan data for the high and low cell constants respectively. On each plot are shown the raw suspension scans (circles) along with their equivalent polarisation controls (squares). Conventional polarisation controls were applied to the data by subtracting the polarisation control data from the suspension data. The polarisation control data's capacitance at 1 MHz was added back to the resulting curves to allow them to be plotted in comparison with the original data (triangles). From FIG. 20A and B it can be seen that this has largely eliminated the polarisation tip-up at low frequencies. The problem with polarisation controls is that they also compensate for the sloping BM baseline and the high-frequency inductance effects. This explains why the data compensated using them have a different shape at higher frequencies. The 2f method does not compensate the baseline slopes or the high frequency inductances and so a better way of comparing data would be to extract just the polarisation component from the polarisation control data and subtract this from cell suspension data. This can be done by using the power law fits to the polarisation in the polarisation's control data (as was done in FIGS. 3 and 4) to generate data values at each frequency used, as was done on FIG. 5. These data can then be subtracted from the raw cell suspension date. The resulting plots are also shown on FIGS. 20A and B (thick line). As would be expected, they follow the conventional polarisation controlled data at low frequencies and follow the cell suspension data at a higher frequencies where the polarisation is no longer seen.

The final set of data was obtained by applying the 2f method of removing electrode polarisation to the raw cell suspension data using a $^Lf$ and $^hf$ of 0.2 and 0.28 MHz respectively, exactly as described before (thin line). For both FIGS. 20A and B the differences between the three sets of polarisation compensated data at low frequencies is quite small. None of the compensation methods can be regarded as the "gold standard" as they all involve approximations. For those methods using measured polarisation control data the subtraction process is applying to a serial combination of electrode impedance and suspension impedance a method strictly applicable only to a parallel arrangement of these two impedances. The method only works well because of the fortuitous values these impedances take for typical electrode/suspension systems. Thus some error is to be expected. The fact that the baseline of the BM slopes down and that the β-dispersion of the yeast will also produce a sloping offset suggests, from the analysis of sloping offsets earlier, that the real polarisation-free curve may plateau slightly above the 2f method's curves shown. In any case all the polarisation compensated data do appear by eye to fit well with the breakpoint in the suspension data at about 1 MHz, below which the polarisation causes the curve to tip-up.

Modifications to the 2f method.

For most situations the 2f method of electrode polarisation reduction will work well and has the virtue of simplicity. There may be times however when a sloping offset could produce severe problems for biomass measurements, and frequency scans in particular. Under these conditions the 2f method could be enlarged to a three frequency method which would model the offset as a sloping straight line with the offset capacitances at the three frequencies sitting on it. Similar simultaneous equations (equivalent to Equations 6–9) as used in the 2f method could then be solved to allow for this slope. The three frequencies would need to be close together to ensure that the offset capacitances do lie roughly on a straight line and such a method may be easier to derive using p directly rather than using constant $^Lf$ and $^hf$ values and, say, an equivalent three quarters frequency.

For situations where the $^hf$ and $^LC_p$ are both variable, a 3 frequency method could be used that assumed that the offset capacitance was constant at the three frequencies. The simultaneous equations for $^hf$ and $^LC_p$ could then be solved.

Four or more frequencies could also be used if one wished to model the changing offset under the polarisation curve by a more complex and realistic function.

Concluding remarks

We have shown that the electrode polarisation exhibited in aqueous ionic media follows a power law model and this is in line with work on other electrode types on different machines by different groups. The parameters of this model were modified to give reliable and intuitive measures of the magnitude ($^LC_p$) and rate of fall of polarisation with increasing frequency ($^hf$). For the BM it was shown that although the magnitude of electrode polarisation depends strongly on the conductance of the medium and the material of the electrodes, above a certain value of medium conductance (of some 3–7 mS, 3.7–8.7 mS.cm$^{-1}$) the value of $^hf$ is a constant and independent of the conductance of the medium. It is also independent of the electrode metal in the probes, which probe was used, the ionic and other components in the medium, the electrode interface current density, the cell constant, the presence of fouling materials and whether or not any electrolytic cleaning pulses had been applied.

A useful consequence of the constant $^hf$ for the BM is that spot measurements at two frequencies can be used to compensate for electrode polarisation using the 2f method described above. This method was shown by simulation and with real suspensions to provide reliable biomass measurements even when its key assumption of a constant offset was violated. For practical applications, a spot biomass measuring frequency would be used which was higher than the two frequencies used by the 2f method, to reduce any errors caused by the non-constant offset. For most practical situations the 2f method would seem to provide as good a removal of electrode polarisation on frequency scans as conventional polarisation control methods give. For cases where a sloping offset causes sever problems modifications of the 2f method using 3 or more frequencies may be used.

To use the 2f method the polarisation must follow a power law and have a constant known $^hf$ value. If these requirements are met the technique can be applied to any electrode system, not just those of the BM, and the equations were derived so that they were not absolutely specific to the BM. If the $^hf$ is known to move then one of the modified forms of the 2f model using three or more frequencies may be used.

Applied to the current range of BMs, the 2f method is easy to implement on a controlling computer and the stability of the $^hf$ value means that experiment-by-experiment recalibration would not be required. Once implemented the results would be on-line, real-time, relatively resistant to noise and would require no expert intervention from the users.

Referring now to FIG. 24, from the foregoing description, those skilled in the art will appreciate that an apparatus 100 for performing the methods of the invention will include two electrodes 102, 104, coupled to a capacitance measurement means 106 and a frequency selection means 108. A ratio divider 110 is coupled to the capacitance measurement means 106 for finding the ratio of measurements and providing an ratio output 112.

TABLE 1

| mM KCl | Part 1 order | Part 2 order | Part 3 order |
|--------|--------------|--------------|--------------|
| 10     | 1st          | —            | —            |
| 19     | —            | 2nd          | —            |
| 28     | —            | —            | 7th          |
| 38     | 2nd          | —            | —            |
| 47     | —            | 3rd          | —            |
| 56     | —            | —            | 2nd          |
| 65     | 6th          | —            | —            |
| 74     | —            | 1st          | —            |
| 83     | —            | —            | 5th          |
| 93     | 5th          | —            | —            |
| 102    | —            | 7th          | —            |
| 111    | —            | —            | 4th          |
| 120    | 4th          | —            | —            |
| 129    | —            | 4th          | —            |
| 138    | —            | —            | 3rd          |

TABLE 1-continued

| mM KCl | Part 1 order | Part 2 order | Part 3 order |
|---|---|---|---|
| 148 | 3rd | — | — |
| 157 | — | 6th | — |
| 166 | — | — | 8th |
| 175 | 7th | 5th | 1st and 6th |

Appendix 1. Getting $^h f$ from p

The problem with the linear fit to a log/log plot like FIG. (4) is that the line has the form of Equation (2) which uses the polarisation capacitance at 1 Hz ($^{1Hz}C_p$) as a reference point. To calculate $^h f$ we need to restate the fitted line in a form that uses $^L f$ as its reference point. The way one does this is to restate the general equation for a straight line in the form given by Equation (A1.1):

$$y_2 = y_1 + \text{slope } (x_2 - x_1) \tag{A1.1}$$

The y and x terms refer to the y- and x-axes respectively. The two points referred to have subscripts 1 and 2 to identify them, with the 2 terms being at the higher x value. By inspection one can make a log/log plot like FIG. (4) fit this form of a straight line by using $^L f$ and an arbitrary frequency f as the x-axis values, to give upon rearrangement:

$$\log(^f C_p) = \log(^L C_p) + p \log(f/L_f) \tag{A1.2}$$

By definition the capacitance due to electrode polarisation at the half frequency is $^L C_p/2$. Substituting $^h f$ for f and $^L C_p/2$ for $^f C_p$ in Equation (A1.2) gives upon rearrangement:

$$-\log(2) = p \log(^h f/L_f) \tag{A1.3}$$

Anti-logging both sides and then rearranging gives Equation (5).

Appendix 2. Calculating the Frequency Dependence of the Polarisation

Equation (A1.3) is rearranged for p and then substituted into Equation (A1.2); which is the alternative form of the linearised power law, to give:

$$\log(^f C_p) = \log(^L C_p) - \frac{\log(2)}{\log\left(\frac{hf}{Lf}\right)} \log\left(\frac{f}{Lf}\right) \tag{A2.1}$$

Anti-logging both sides and simplifying gives Equation (9).

Appendix 3. An Error Function for the 2f Method

On FIG. (17) it was shown that if the offset under the polarisation curve sloped between $^L f$ and $^h f$ (in the case shown, sloped down) then the 2f method does not give the correct polarisation curve as a function of frequency. Infact instead of getting the correct curve of FIG. 17 line (d) one gets curve (e). The aim of this appendix is to derive an equation that explicitly states the frequency dependent difference between lines (e) and (d) as a percentage of the correct values (line (d)) interms of the change in the offset capacitance between $^L f$ and $^h f$.

Equation (10) states this frequency dependent error ($^f E_p$). Each of the $^f C_p$ terms in this equation has the form of Equation (9) with the same values of $^L f$ and $^h f$ because these values are assumed to be known constants when using the 2f model. This inturn means that the power of 2 terms in Equation (9) are the same with and without the offset error. What differs between the polarisation curves with and without offset error is the magnitude of the $^L C_p$ the 2f model gives. FIG. 21 shows lines (d) and (e) from FIG. (17) in more detail, with the notation used in these derivations. The thick line is the correct polarisation curve and has the correct $^L C_p$ and $^f C_p$ values. The thin line curve represents the polarisation curve the 2f model gives when the offset is not constant between $^L f$ and $^h f$ (i.e. with offset error present). The additional "a,Δo" terms in the subscripts indicate that the values are (calculated) apparent values due to the change in the offset capacitance. From these arguments one can see that the "$^f C_p$ without offset error" terms in Equation (10) can be replaced by Equation (9). The "$^f C_p$ with offset error" terms are replaced by the modified form of Equation (9):

$$^f C_{p,a\Delta o} = {}^L C_{p,a\Delta o} 2^{(\log(Lf/f)/\log(hf/Lf))} \tag{A3.1}$$

To calculate the $^f C_{p,a\Delta o}$ to inset into Equation (10) one needs to find a equation for $^L C_{p,a\Delta o}$ which includes the change in the offset capacitance between $^L f$ and $^h f$.

Finding an equation for $^L C_{p,a\Delta o}$

FIG. 22 shows the segment of a cell suspension's capacitance plot between $^L f$ and $^h f$ with the offset capacitances being equal at the two frequencies. From this situation one may vary the offset capacitances in four ways: keep $^L C_o$ constant and increase or decrease $^h C_o$, or keep $^h C_o$ constant and increase and decrease $^L C_o$.

Taking first the case where $^L C_o$ is held constant. FIG. 23 shows what happens to FIG. 22 when the $^h C_o$ is lowered. The true $^L C_p$ and $^L C_p/2$ values are the same, what changes are the measured capacitance values. These values are flagged to show that they pertain to the situation of a changing offset (between $^L f$ and $^h f$) by having "Δo" appended to their subscripts. Thus the capacitances a BM would measure under these conditions is called $^f C_{m,\Delta o}$ and the spot capacitances at $^L f$ and $^h f$ are called $^L C_{m,\Delta o}$ and $^h C_{m,\Delta o}$ respectively. One defines the change in the offset capacitance between $^L f$ and $^h f$ as the $\Delta C_o$ shown on FIG. This is given by Equation (11).

From FIG. 23 we see that the measured capacitance at $^L f$ is given by:

$$^L C_{m,\Delta o} = {}^L C_o + {}^L C_p \tag{A3.2}$$

The measured capacitance at $^h f$ is given by:

$$^h C_{m,\Delta o} = {}^L C_o + \Delta C_o + \frac{^L C_p}{2} \tag{A3.3}$$

Infact both Equations (A3.2) and (A3.3) also apply to the situation where $^L C_o$ is constant but $^h C_o$ is increased. Next one subtracts Equation (A3.3) from (A3.2) to give:

$$^L C_{m,\Delta o} - {}^h C_{m,\Delta o} = \frac{^L C_p}{2} - \Delta C_o \tag{A3.4}$$

Next we repeat the above procedure for the case where the $^h C_o$ is constant but the $^L C_o$ is either increased or decreased. Once again the derived equations for the measured capacitances at these two spot frequencies apply in both cases and are:

$$^L C_{m,\Delta o} = {}^h C_o + (-\Delta C_o) + {}^L C_p \tag{A3.5}$$

$$^h C_{m,\Delta o} = {}^h C_o + \frac{^L C_p}{2} \tag{A3.6}$$

Subtracting Equation (A3.6) from (A3.5) once again gives Equation (A3.4). Thus one can use Equation (A3.4) for all the possible situations where the offset changes between $^L f$ and $^h f$.

In reality when we make a 2f method measurement we measure $^L C_m$ and $^h C_m$ at $^L f$ and $^h f$ and insert these values into the Equation (8); which assumed no offset changes (error), to get the correct value of $^L C_p$. Now if an offset error was present we would again just take spot capacitance readings at $^L f$ and $^h f$ to give this time $^L C_{m,\Delta o}$ and $^h C_{m,\Delta o}$. Inserting these values into Equation (8) instead of $^L C_m$ and $^h C_m$ gives:

$$^L C_{p,a\Delta o} = 2(^L C_{m,\Delta o} - {^h C_{m,\Delta o}}) \quad (A3.7)$$

The estimated $^L C_p$ is now called $^L C_{p,a\Delta o}$ (see FIG. 21 to remind us that the calculated $^L C_p$ is an apparent one due to errors caused by changes in the offset capacitances which we have not allowed for by blindly using the 2f model. One can replace the bracketed terms in Equation (A3.7) by substituting in Equation (A3.4) to give:

$$^L C_{p,a\Delta o} = 2\left(\frac{^L C_p}{2} - \Delta C_o\right) \quad (A3.8)$$

We know have an explicit statement of $^L C_{p,a\Delta o}$ to insert into Equation (A3.1) to give:

$$^f C_{p,a\Delta o} = 2\left(\frac{^L C_p}{2} - \Delta C_o\right) 2^{(\log(^L f : f)/\log(^h f \cdot ^L f))} \quad (A3.9)$$

Calculating $^f E_p$.

Equation (10) gives an explicit statement of $^f E_p$. Its "$^f C_p$ without offset error" terms can be replaced by Equation (9) while the "$^f C_p$ with offset error" terms are replaced by Equation (A3.9). Making these substitutions into Equation (10) and then simplifying gives Equation (12).

What is claimed is:

1. A method for analyzing a dielectric medium, said method comprising the steps of:
    measuring, at a test frequency, the capacitance between a pair of electrodes immersed in the dielectric medium, a portion of the capacitance measurement being due to electrode polarization capacitance; and
    determining either the proportion of said capacitance measurement due to said electrode polarization capacitance or the proportion of said capacitance measurement due to the residual capacitance of the dielectric medium, wherein
    either of said proportions is determined using a first capacitance measurement made between said electrodes at a first frequency and a second capacitance measurement made between said electrodes at a second frequency, the values of the first and second frequencies being chosen such that the ratio of the respective electrode polarization capacitance values at those frequencies is known,
    said first and second measurement frequencies lie within a range over which said residual capacitance level is assumed to be substantially constant,
    said capacitance measurements made at said first and second measurement frequencies are used to calculate the respective electrode polarization capacitances at said first and second measurement frequencies, and
    the calculated electrode polarization capacitances at said first and second measurement frequencies are substituted in turn into the equation Cpol=Af$^p$ (where Cpol is the electrode polarization capacitance at frequency f, and A and p are constants), the resulting equations being solved simultaneously to obtain an expression for estimating electrode polarization capacitance at any frequency.

2. A method as claimed in claim 1, wherein said capacitance measurements made at said first and second measurement frequencies are used to calculate said residual capacitance.

3. A method as claimed in claim 2, wherein said dielectric medium is a biomass medium said calculated residual capacitance is used to establish the biomass content of said medium.

4. A method as claimed in claim 1, wherein the conductance of said dielectric medium lies within a range over which the value of p in the equation Cpol=Af$^p$ (where Cpol is the electrode polarization capacitance at frequency f, and A and p are constants) is assumed to be substantially constant.

5. A method as claimed in claim 1, wherein said first and second measurement frequencies lie within a range over which said residual capacitance level is assumed to vary substantially linearly with frequency, and either of said proportions is determined using capacitance measurements made between said electrodes at said first and second frequencies and at one or more additional frequencies.

6. A method for analyzing a dielectric medium, said method comprising the steps of:
    measuring, at a test frequency, the capacitance between a pair of electrodes immersed in the dielectric medium, a portion of the capacitance measurement being due to electrode polarization capacitance; and
    determining either the proportion of said capacitance measurement due to said electrode polarization capacitance or the proportion of said capacitance measurement due to the residual capacitance of the dielectric medium, wherein
    either of said proportions is determined using a first capacitance measurement made between said electrodes at a first frequency and a second capacitance measurement made between said electrodes at a second frequency, the values of the first and second frequencies being chosen such that the ratio of the respective electrode polarization capacitance values at those frequencies is known, and
    the conductance of said dielectric medium lies within a range over which the value of p in the equation Cpol=Af$^p$ (where Cpol is the electrode polarization capacitance at frequency f, and A and p are constants) is assumed to be substantially constant.

7. A method as claimed in claim 6, wherein said first and second measurement frequencies lie within a range over which said residual capacitance level is assumed to be substantially constant.

8. A method as claimed in claim 7, wherein said capacitance measurements made at said first and second measurement frequencies are used to calculate said residual capacitance.

9. A method as claimed in claim 8, wherein said dielectric medium is a biomass medium said calculated residual capacitance is used to establish the biomass content of said medium.

10. A method as claimed in claim 6, wherein the value of p is estimated from experimental data obtained for a control medium.

11. A method as claimed in claim 6, wherein appropriate values for said first and second measurement frequencies are determined by estimating, for a control medium, the polarization capacitance at a first measurement frequency, and then varying the measurement frequency to identify the frequency at which the estimated polarization capacitance for that control medium has varied by a predetermined amount.

12. A method as claimed in claim 6, wherein said first and second measurement frequencies lie within a range over which said residual capacitance level is assumed to vary substantially linearly with frequency, and either of said proportions is determined using capacitance measurements made between said electrodes at said first and second frequencies and at one or more additional frequencies.

13. An apparatus for measuring, at a test frequency, the capacitance between a pair of electrodes immersed in a dielectric medium, a portion of the capacitance measurement being due to electrode polarization capacitance, and for determining either the proportion of said capacitance measurement due to said electrode polarization capacitance or the proportion of said capacitance measurement due to the residual capacitance of the dielectric medium, wherein either of said proportions is determined using a first capacitance measurement made between said electrodes at a first frequency and a second capacitance measurement made between said electrodes at a second frequency, the values of the first and second frequencies being chosen such that the ratio of the respective electrode polarization capacitance values at those frequencies is known, the apparatus is arranged to calculate the respective electrode polarization capacitances at said first and second measurement frequencies, and the apparatus is arranged to substitute the calculated electrode polarization capacitances at said first and second measurement frequencies in turn into the equation $Cpol = Af^p$ (where Cpol is the electrode polarization capacitance at frequency f, and A and p are constants), and to solve the resulting equations simultaneously to obtain an expression for estimating electrode polarization capacitance at any frequency.

14. An apparatus as claimed in claim 13, arranged to calculate said residual capacitance.

15. An apparatus as claimed in claim 13, arranged to estimate the value of p in the equation $Cpol = Af^p$ (where Cpol is the electrode polarization capacitance at frequency f, and A and p are constants), from experimental data obtained for a control medium.

16. An apparatus for measuring, at a test frequency, the capacitance between a pair of electrodes immersed in a dielectric medium, a portion of the capacitance measurement being due to electrode polarization capacitance, and for determining either the proportion of said capacitance measurement due to said electrode polarization capacitance or the proportion of said capacitance measurement due to the residual capacitance of the dielectric medium, wherein either of said proportions is determined using a first capacitance measurement made between said electrodes at a first frequency and a second capacitance measurement made between said electrodes at a second frequency, the values of the first and second frequencies being chosen such that the ratio of the respective electrode polarization capacitance values at those frequencies is known, and the apparatus is arranged to estimate the value of p in the equation $Cpol = Af^p$ (where Cpol is the electrode polarization capacitance at frequency f, and A and p are constants), from experimental data obtained for a control medium.

17. An apparatus as claimed in claim 16, arranged to calculate said residual capacitance.

18. An apparatus as claimed in claim 16, arranged to calculate the respective electrode polarization capacitances at said first and second measurement frequencies.

19. An apparatus as claimed in claim 16, arranged to determine appropriate values for said first and second measurement frequencies by substituting said estimated value of p into said equation.

* * * * *